(12) United States Patent
Huang et al.

(10) Patent No.: US 9,290,454 B2
(45) Date of Patent: Mar. 22, 2016

(54) SUBSTITUTED ISOQUINOLINES AS CRTH2 RECEPTOR MODULATORS

(71) Applicant: Merck Sharp & Dohme Corp., Rahway, NJ (US)

(72) Inventors: Xianhai Huang, Warren, NJ (US);
Anandan Palani, Bridgewater, NJ (US);
Ashwin U. Rao, Morganville, NJ (US);
Hongjun Zhang, Newton, MA (US);
Wei Zhou, Scotch Plains, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/432,462

(22) PCT Filed: Sep. 26, 2013

(86) PCT No.: PCT/US2013/061786
§ 371 (c)(1),
(2) Date: Mar. 30, 2015

(87) PCT Pub. No.: WO2014/055311
PCT Pub. Date: Apr. 10, 2014

(65) Prior Publication Data
US 2015/0353498 A1     Dec. 10, 2015

Related U.S. Application Data

(60) Provisional application No. 61/708,327, filed on Oct. 1, 2012.

(51) Int. Cl.
| | |
|---|---|
| *C07D 413/04* | (2006.01) |
| *C07D 401/06* | (2006.01) |
| *C07D 217/24* | (2006.01) |
| *A61K 31/472* | (2006.01) |
| *A61K 31/496* | (2006.01) |
| *A61K 31/4725* | (2006.01) |
| *C07D 413/14* | (2006.01) |

(52) U.S. Cl.
CPC ............ *C07D 217/24* (2013.01); *A61K 31/472* (2013.01); *A61K 31/4725* (2013.01); *A61K 31/496* (2013.01); *C07D 401/06* (2013.01); *C07D 413/04* (2013.01); *C07D 413/14* (2013.01)

(58) Field of Classification Search
None
See application file for complete search history.

(56) References Cited

U.S. PATENT DOCUMENTS

| | | | |
|---|---|---|---|
| 8,394,819 B2 | 3/2013 | Berthelette et al. | |
| 8,592,383 B2 | 11/2013 | Huang et al. | |
| 8,927,559 B2 | 1/2015 | Aslanian et al. | |
| 2002/0058644 A1 | 5/2002 | Leblanc et al. | |
| 2004/0097499 A1 | 5/2004 | Arnold et al. | |
| 2009/0326008 A1 | 12/2009 | Ishiyama et al. | |
| 2011/0071178 A1 | 3/2011 | Makriyannis et al. | |
| 2012/0157454 A1 | 6/2012 | Papeo et al. | |
| 2013/0296300 A1 | 11/2013 | Boyce et al. | |
| 2013/0303517 A1 | 11/2013 | Boyce et al. | |

FOREIGN PATENT DOCUMENTS

| | | |
|---|---|---|
| WO | WO2005077343 A2 | 8/2005 |
| WO | WO2011146882 A1 | 11/2011 |

OTHER PUBLICATIONS

Ishihara, Y. et al., "Synthesis of Isoindolo[2,1-a]quinoline Derivatives and Their Effects on N2-Induced Hypoxia", Chemical Pharmaceutical Bulletin, 1990, p. 3024-3030, vol. 38(11).

Nishijima, K. et al., "Synthesis and diuretic activity of 4,5-dihydro-6H-imidazo[4,5,1-ij]quinoline-6-one 6-oxime—O—sulfonic acid derivatives", European Journal of Medicinal Chemistry, 1998, p. 763-774, vol. 33(10).

Chem Abstract 1980:128693 of MODI, A.R. et al., "Isoquinolones. Part IV. Synthesis of 3-methyl, 3-formyl, and other 3-substituted N-arylisoquinolones", Indian Journal of Chemistry, Section B: Organic Chemistry Including Medicinal Chemistry, 1979, vol. 18B(4), p. 304-306.

International Search Report and Written Opinion of PCT/US2013/61786 mailed Feb. 7, 2014.

*Primary Examiner* — Zinna Northington Davis
(74) *Attorney, Agent, or Firm* — Eric A. Meade; Catherine D. Fitch

(57) ABSTRACT

The invention provides certain substituted isoquinolines of the Formula (I), and their pharmaceutically acceptable salts and esters. The invention also provides pharmaceutical compositions comprising such compounds, and methods of using the compounds for treating diseases or conditions associated with uncontrolled or inappropriate stimulation of CRTH2 function.

19 Claims, No Drawings

SUBSTITUTED ISOQUINOLINES AS CRTH2 RECEPTOR MODULATORS

CROSS REFERENCE TO RELATED APPLICATIONS

This application is a U.S. National Phase application under 35 U.S.C. §371 of PCT Application No. PCT/US2013/061786, filed Sep. 26, 2013, which claims priority under 35 U.S.C. §119(e) from U.S. Provisional Application No. 61/708,327, filed Oct. 1, 2012.

FIELD OF THE INVENTION

The present invention relates to certain substituted isoquinolines of the Formula (I) (also referred to herein as the "compounds of the Formula (I)"), compositions comprising such compounds, and methods of using such compounds for treating an inflammatory disease, or other disorder mediated by the chemoattractant receptor-homologous molecule expressed on T-helper-type-2 cells ($CRTH_2$).

BACKGROUND OF THE INVENTION

Prostaglandin $D_2$ ($PGD_2$) belongs to a class of chemical mediators which cells synthesize in response to stimuli, such as local tissue damage or hormonal stimuli, or by cellular activation pathways. Cells synthesize $PGD_2$ from arachidonic acid by cyclooxygenase and other specific synthases in the pathway.

Upon stimulation, mast cells release $PGD_2$ in major amounts and this release plays a major role in the etiology of respiratory disease, such as asthma and congestion. $PGD_2$ achieves this effect by binding with either of two G-protein coupled receptors, which are the D-prostanoid (DP) receptor and the $CRTH_2$ receptor. TH-2 cells, eosinophils, and basophils express the $CRTH_2$ receptor, which mediates the chemoattractant effect of $PGD_2$.

Scientific studies support a clear role for $PGD_2$ in an allergic inflammatory response. $PGD_2$ is found at high levels in the bronchoalveolar lavage of asthmatics. Inhalation of $PGD_2$ enhances eosinophilic and lymphocytic airway inflammation in allergic animal models. Evidence obtained by studying $CRTH_2$ knockout mice demonstrates that $PGD_2$ achieves this enhancement by binding to the $CRTH_2$ receptor. Hence, $CRTH_2$ receptor antagonists would be expected to reduce the allergic inflammatory response caused by $PGD_2$, and these compounds would be useful in the treatment or prevention of allergic/immune disorders.

Current drugs of choice for the treatment of chronic inflammatory airway disease, such as asthma or COPD, are synthetic glucocorticoids; examples of these compounds currently indicated for treating these disorders include fluticasone and mometasone. The difficulty with treating patients with this class of compounds is that the compounds possess a number of systemic side-effects; these include adrenal suppression, altered bone metabolism and growth suppression in children. These side effects limit the dose that can be administered on a daily basis to the patient. While a non-steroidal class of therapeutics that inhibit bronchoconstriction exists ($CysLT_1$ antagonists), this class of compounds has limited efficacy in achieving the endpoints of reducing inflammatory and improving in lung function when compared to the glucocorticoids. Therefore, a therapeutic that combines the efficacy of inhaled glucocorticoids without the side effects would be advantageous.

SUMMARY OF THE INVENTION

The present invention provides novel compounds of the Formula (I) as described below and pharmaceutically acceptable salts or esters thereof as well as pharmaceutical compositions containing them. The compounds of Formula (I) are useful in the treatment and prevention of diseases and disorders associated with uncontrolled or inappropriate stimulation of $CRTH_2$ function such as asthma.

DETAILED DESCRIPTION OF THE INVENTION

Definitions

The terms used herein have their ordinary meaning and the meaning of such terms is independent at each occurrence thereof. That notwithstanding and except where stated otherwise, the following definitions apply throughout the specification and claims. Chemical names, common names, and chemical structures may be used interchangeably to describe the same structure. If a chemical compound is referred to using both a chemical structure and a chemical name, and an ambiguity exists between the structure and the name, the structure predominates. These definitions apply regardless of whether a term is used by itself or in combination with other terms, unless otherwise indicated. Hence, the definition of "alkyl" applies to "alkyl" as well as the "alkyl" portions of "hydroxyalkyl," "fluoroalkyl," "—O-alkyl," etc.

As used herein, and throughout this disclosure, the following terms, unless otherwise indicated, shall be understood to have the following meanings:

A "patient" is a human or non-human mammal. In one embodiment, a patient is a human. In another embodiment, a patient is a chimpanzee.

The term "therapeutically effective amount" as used herein, refers to an amount of the compound of Formula (I) and/or an additional therapeutic agent, or a composition thereof that is effective in producing the desired therapeutic, ameliorative, inhibitory or preventative effect when administered to a patient suffering from a disease or condition associated with uncontrolled or inappropriate stimulation of $CRTH_2$ function. In the combination therapies of the present invention, a therapeutically effective amount can refer to each individual agent or to the combination as a whole, wherein the amounts of all agents administered are together effective, but wherein the component agent of the combination may not be present individually in an effective amount.

The term "preventing," as used herein with respect to disease or disorder associated with uncontrolled or inappropriate stimulation of $CRTH_2$ function, refers to reducing the likelihood of the occurrence of such disease or disorder.

The term "alkyl," as used herein, refers to an aliphatic hydrocarbon group having one of its hydrogen atoms replaced with a bond having the specified number of carbon atoms. In different embodiments, an alkyl group contains from 1 to 6 carbon atoms ($C_1$-$C_6$ alkyl) or from 1 to 3 carbon atoms ($C_1$-$C_3$ alkyl). Non-limiting examples of alkyl groups include methyl, ethyl, n-propyl, isopropyl, n-butyl, sec-butyl, isobutyl, tert-butyl, n-pentyl, neopentyl, isopentyl, n-hexyl, isohexyl and neohexyl. In one embodiment, an alkyl group is linear. In another embodiment, an alkyl group is branched.

The term "fluoroalkyl," as used herein, refers to an alkyl group as defined above, wherein one or more of the alkyl group's hydrogen atoms has been replaced with a fluorine. In one embodiment, a fluoroalkyl group has from 1 to 6 carbon atoms. In another embodiment, a fluoroalkyl group has from 1 to 3 carbon atoms. In another embodiment, a fluoroalkyl group is substituted with from 1 to 3 F atoms. Non-limiting examples of fluoroalkyl groups include —CH$_2$F, —CHF$_2$, and —CF$_3$. The term "C$_1$-C$_3$ fluoroalkyl" refers to a fluoroalkyl group having from 1 to 3 carbon atoms.

The term "alkoxy" as used herein, refers to an —O-alkyl group, wherein an alkyl group is as defined above. Non-limiting examples of alkoxy groups include methoxy, ethoxy, n-propoxy, isopropoxy, n-butoxy and t-butoxy. An alkoxy group is bonded via its oxygen atom to the rest of the molecule.

The term "aryl," as used herein, refers to an aromatic monocyclic or multicyclic ring system comprising from about 6 to about 14 carbon atoms. In one embodiment, an aryl group contains from about 6 to 10 carbon atoms (C$_6$-C$_{10}$ aryl). In another embodiment an aryl group is phenyl. Non-limiting examples of aryl groups include phenyl and naphthyl.

The term "carbocycle," as used herein, refers to a fully saturated, partially unsaturated, or an aromatic monocyclic or multicyclic ring system comprising from about 6 to 14 carbon atoms. In one embodiment, an aryl group contains from 3 to 10 carbon atoms (C$_3$-C$_{10}$ carbocycle). Non-limiting examples of carbocyclic groups include cycloalkyl and aryl groups, as defined herein. In specific embodiments, the carbocylic groups are selected from cyclopropyl, cyclobutyl, cyclopentyl, cyclohexyl, phenyl, indanyl, napthyl, and tetrahydronapthyl.

The term "cycloalkyl," as used herein, refers to a saturated ring containing the specified number of ring carbon atoms, and no heteroatom. In a like manner the term "C$_3$-C$_6$ cycloalkyl" refers to a saturated ring having from 3 to 6 ring carbon atoms. Non-limiting examples of monocyclic cycloalkyls include cyclopropyl, cyclobutyl, cyclopentyl, and cyclohexyl.

The term "halo," as used herein, means —F, —Cl, —Br or —I. In one embodiment, a halo group is —F or —Cl. In another embodiment, a halo group is —F.

The term "heteroaryl," as used herein, refers to an aromatic monocyclic or multicyclic ring system comprising about 5 to about 14 ring atoms, wherein from 1 to 3 of the ring atoms is independently N, O, or S and the remaining ring atoms are carbon atoms. In one embodiment, a heteroaryl group has 5 to 10 ring atoms. In another embodiment, a heteroaryl group is monocyclic ring system and has 5 or 6 ring atoms. In another embodiment, a heteroaryl group is a bicyclic ring system. A heteroaryl group is joined via a ring carbon atom. The term "heteroaryl" also includes a heteroaryl as defined above fused to a heterocyclyl as defined below. The term "heteroaryl" also encompasses a heteroaryl group, as defined above, which is fused to a benzene, a cyclohexadiene or a cyclohexene ring. Non-limiting examples of heteroaryls include pyridyl, pyrazinyl, furanyl, thienyl, pyrimidinyl, pyridone (including N-substituted pyridones), isoxazolyl, isothiazolyl, oxazolyl, oxadiazolyl, thiazolyl, pyrazolyl, furyl, pyrrolyl, triazolyl, 1,2,4-thiadiazolyl, pyrazinyl, pyridazinyl, indolyl, quinoxalinyl, phthalazinyl, oxindolyl, imidazo[1,2-a]pyridinyl, imidazo[2,1-b]thiazolyl, and the like. In one embodiment, a heteroaryl group is a 5-membered heteroaryl. In another embodiment, a heteroaryl group is a 6-membered heteroaryl.

The term "heterocyclyl," as used herein, refers to a non-aromatic saturated or partially saturated monocyclic or multicyclic ring system containing 3 to 11 ring atoms, wherein from 1 to 4 of the ring atoms are independently O, S, or N, and the remainder of the ring atoms are carbon atoms. In one embodiment, a heterocyclyl group is monocyclic and has from 3 to 7 ring atoms. In another embodiment, a heterocyclyl group is monocyclic and has from about 4 to 7 ring atoms. In another embodiment, a heterocyclyl group is bicyclic and has from 7 to 11 ring atoms. In still another embodiment, a heterocyclyl group is monocyclic and has 5 or 6 ring atoms. In one embodiment, a heterocyclyl group is monocyclic. In another embodiment, a heterocyclyl group is bicyclic. A heterocyclyl group can be joined to the rest of the molecule via a ring carbon or ring nitrogen atom. The nitrogen or sulfur atom of the heterocyclyl can be optionally oxidized to the corresponding N-oxide, S-oxide or S,S-dioxide. Non-limiting examples of monocyclic heterocyclyl rings include oxetanyl, piperidyl, pyrrolidinyl, piperazinyl, morpholinyl, thiomorpholinyl, thiazolidinyl, dihydropyranyl, pyran, 1,4-dioxanyl, tetrahydrofuranyl, tetrahydrothiophenyl, delta-lactam, delta-lactone, and the like.

In one embodiment, a heterocyclyl group is a 5- to 6-membered monocyclic heterocyclyl. In another embodiment, a heterocyclyl group is a 5-membered monocyclic heterocyclyl. In another embodiment, a heterocyclyl group is a 6-membered monocyclic heterocyclyl. The term "5- to 6-membered heterocyclyl" refers to a monocyclic heterocyclyl group having from 5 to 6 ring atoms.

The term "substituted" means that one or more hydrogens on the atoms of the designated are replaced with a selection from the indicated group, provided that the atoms' normal valencies under the existing circumstances are not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

When any substituent or variable occurs more than one time in any constituent or the compound of Formula (I), its definition on each occurrence is independent of its definition at every other occurrence, unless otherwise indicated.

The term "in purified form," as used herein, refers to the physical state of a compound after the compound is isolated from a synthetic process (e.g., from a reaction mixture), a natural source, or a combination thereof. The term "in purified form," also refers to the physical state of a compound after the compound is obtained from a purification process or processes described herein or well-known to the skilled artisan (e.g., chromatography, recrystallization and the like), in sufficient purity to be characterizable by standard analytical techniques described herein or well-known to the skilled artisan.

It should also be noted that any carbon as well as heteroatom with unsatisfied valences in the text, schemes, examples and tables herein is assumed to have the sufficient number of hydrogen atom(s) to satisfy the valences.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is H$_2$O.

The compounds of Formula (I) may contain one or more stereogenic centers and can thus occur as racemates, racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. Any formulas, structures or names of compounds described in this specification that do not specify a particular stereochemistry are meant to encompass any and all existing isomers as described above and mixtures thereof in any proportion. When stereochemistry is specified, the invention is meant to encompass that particular isomer in pure form or as part of a mixture with other isomers in any proportion.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula (I) may be atropisomers (e.g., substituted biaryls) and are considered as part of this invention. Enantiomers can also be separated by use of chiral HPLC column.

It is also possible that the compounds of Formula (I) may exist in different tautomeric forms, and all such forms are embraced within the scope of the invention.

All stereoisomers (for example, geometric isomers, optical isomers and the like) of the present compounds (including those of the salts and solvates of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations.

The compounds of Formula (I) can form salts which are also within the scope of this invention. Reference to a compound of Formula (I) herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula (I) contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Such acidic and basic salts used within the scope of the invention are pharmaceutically acceptable (i.e., non-toxic, physiologically acceptable) salts. Salts of the compounds of Formula (I) may be formed, for example, by reacting a compound of Formula (I) with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J of Pharmaceutics* (1986) 33 201-217; Anderson et al, *The Practice of Medicinal Chemistry* (1996), *Academic Press*, New York; and in *The Orange Book* (Food & Drug Administration, Washington, D.C. on their website). These disclosures are incorporated herein by reference.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

The present invention further includes the compounds of Formula (I) in all their isolated forms. For example, the above-identified compounds are intended to encompass all forms of the compounds such as, any solvates, hydrates, stereoisomers, and tautomers thereof.

As used herein, the term "composition" is intended to encompass a product comprising the specified ingredients in the specified amounts, as well as any product which results, directly or indirectly, from combination of the specified ingredients in the specified amounts.

In the compounds of generic Formula (I), the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula (I). For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula (I) can be prepared without undue experimentation by conventional techniques well known to those skilled in the art or by processes analogous to those described in the examples herein using appropriate isotopically-enriched reagents and/or intermediates.

Compounds of the Invention

In embodiment no. 1, the present invention provides a compound of the Formula (I):

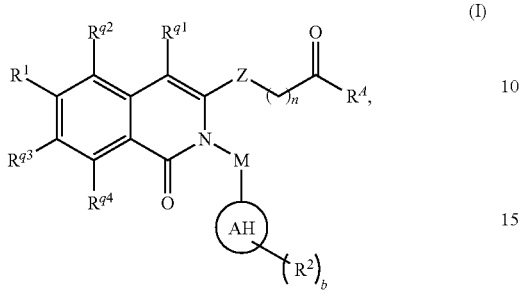

(I)

wherein:

Z is a bond or —N(H)—;

$R^A$ is —OH, —N(H)—S(O)$_2$—$R^{A1}$, or —N(H)—S(O)$_2$—N(H)$R^{A1}$ $R^{A1}$ is $C_1$-$C_6$ alkyl, $C_3$-$C_6$ cycloalkyl, or phenyl, wherein $R^{A1}$ is unsubstituted or substituted by 1 to 3 fluoro or $C_1$-$C_3$ alkyl;

the subscript n is 1, 2, 3, or 4;

M is a bond or $C_1$-$C_3$ alkylene;

ring AH is

A. phenyl; or

B. a 5- to 6-membered heteroaryl containing 1 to 3 heteroatoms selected from the group consisting of N, O, and S;

each $R^2$ is independently selected from the group consisting of halo, $C_1$-$C_3$ alkyl, $C_1$-$C_3$ fluoroalkyl, $C_3$-$C_6$ cycloalkyl, $C_1$-$C_3$ alkoxy, and —CN;

the subscript b is 0, 1, 2, 3, 4, or 5;

$R^{q1}$, $R^{q2}$, $R^{q3}$, and $R^{q4}$ are independently selected from the group consisting of H, halo, and $C_1$-$C_3$ alkyl;

$R^1$ is

A. a group of the formula —C(O)N($R^3$)($R^4$), wherein

1. $R^3$ and $R^4$ are independently (a.) H, or (b.) —Z—$R^{5C}$, wherein

Z is a bond or $C_1$-$C_3$ alkylene;

$R^{5C}$ is (i) $C_5$-$C_{10}$ mono or bicyclic carbocyclyl, (ii.) 5- to 10-membered mono- or bicyclic heterocyclyl containing 1 to 3 heteroatoms selected from N and O;

(iii.) 5- to 10-membered mono or bicyclic heteroaryl containing 1 to 3 heteroatoms selected from N and O;

wherein said carbocyclyl, heterocyclyl, and heteroaryl of $R^{5C}$ is unsubstituted or substituted by 1 to 4 $R^{5A}$ moieties selected from the group consisting of halo, $C_1$-$C_3$ alkyl, $C_1$-$C_3$ fluoroalkyl, $C_1$-$C_3$ alkoxy, and —CN; or 2. $R^3$ and $R^4$ together with the N atom to which they are attached form $R^{5H}$, wherein $R^{5H}$ is selected from the group consisting of:

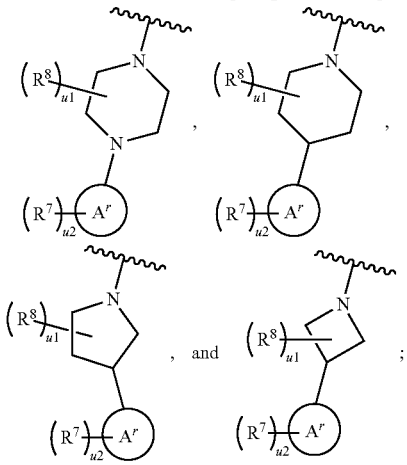

ring g is aryl, pyridyl, or pyrimidyl;

each $R^7$ is independently selected from the group consisting of halo, $C_1$-$C_3$ alkyl, $C_1$-$C_3$ fluoroalkyl, $C_1$-$C_3$ alkoxy, and —CN;

each $R^8$ is independently selected from the group consisting of H and $C_1$-$C_3$ alkyl;

the subscript u1 is 0, 1 or 2;

the subscript u2 is 0, 1, 2, or 3; or

B. a moiety selected from the group consisting of:

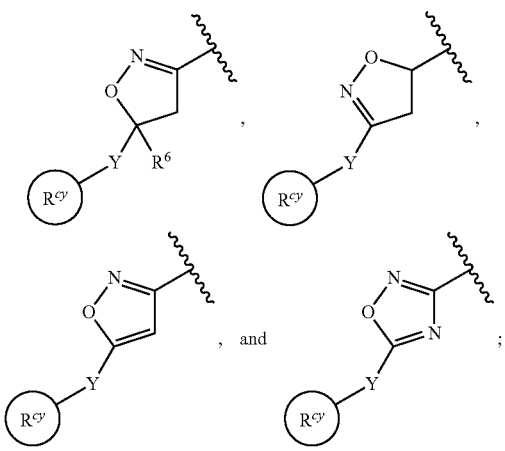

Y is a bond or $C_1$-$C_3$ alkylene;

$R^6$ is H, $C_1$-$C_3$ alkyl, or $C_3$-$C_6$ cycloalkyl;

$R^{cy}$ is:

1. $C_6$-$C_{10}$ mono or bicyclic carbocyclyl;

2. 5- to 9-membered mono- or bicyclic heterocyclyl containing 1 to 3 heteroatoms selected from the group consisting of N and O;

3. 5- to 9-membered mono- or bicyclic heteroaryl containing 1 to 3 heteroatoms selected N and O;

wherein $R^{cy}$ is unsubstituted or substituted by 1 to 3 $R^9$ moieties which are independently selected from the group consisting of halo, $C_1$-$C_3$ alkyl, $C_1$-$C_3$ fluoroalkyl, $C_1$-$C_3$ alkoxy, and —CN, or wherein two $R^9$ moieties are geminally substituted on a common ring carbon of $R^{cy}$, the two geminally substituted $R^9$ moieties, together with said common carbon atom, form —C(O)—;

or a pharmaceutically acceptable salt thereof.

In embodiment no. 2, the invention provides a compound of the Formula (I), wherein $R^1$ is the group of the formula —C(O)N($R^3$)($R^4$), and the remaining variables are as described in embodiment no. 1.

In embodiment no. 3, the invention provides a compound of the Formula (I), wherein A is as described in embodiment no. 1 or 2, $R^3$ is —Z—$R^{5C}$ and $R^4$ is H, and the remaining variables are as described in embodiment no. 1.

In embodiment no. 4, the invention provides a compound of the Formula (I), wherein $R^3$ is —Z—$R^5$ and $R^4$ is H, Z is a bond or

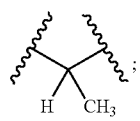

and $R^{5C}$ is $C_6$-$C_{10}$ carbocyclyl, wherein said $C_6$-$C_{10}$ carbocyclyl is unsubstituted or substituted by 1 to 4 $R^{5A}$ moieties; and the remaining variables are as described in embodiment no. 1

In embodiment no. 5, the invention provides a compound of the Formula (I), wherein $R^3$ and $R^4$ are as described in embodiment no. 4, and said $C_6$-$C_{10}$ carbocyclyl of $R^{5c}$ is selected from the group consisting of phenyl, indanyl or tetrahydronaphthalenyl.

In embodiment no. 6, the invention provides a compound of the Formula (I), wherein $R^1$ is as described in embodiment no. 1 or 2, and $R^3$ and $R^4$ together with the N atom to which they are attached form $R^{5H}$; and the remaining variables are as described as in embodiment no. 1.

In embodiment no. 7, the invention provides a compound of the Formula (I), wherein $R^1$ is as described in embodiment no. 1 or 2;

$R^3$ and $R^4$ together with the N atom to which they are attached form $R^{5H}$, $R^{5H}$ is

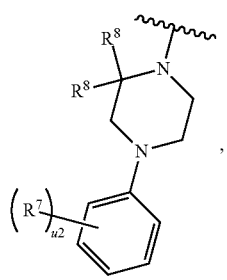

and the remaining variables are as described in embodiment no. 1.

In embodiment no. 8, the invention provides a compound of the Formula (I), wherein $R^1$ is a moiety selected from the group consisting of:

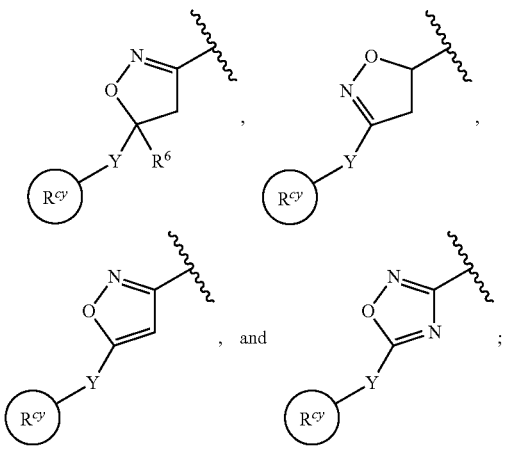

and the remaining variables are as described in embodiment no. 1.

In embodiment no. 9, the invention provides a compound of the Formula (I), wherein $R^1$ is a moiety selected from the group consisting of:

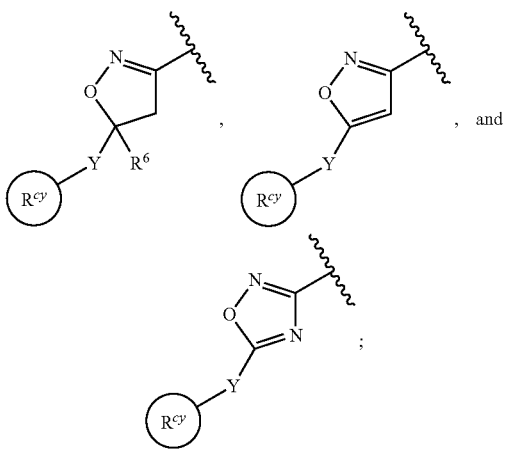

and the remaining variables are as described in embodiment no. 1.

In embodiment no. 10, the invention provides a compound of the Formula (I), wherein $R^1$ is as described in embodiment nos. 8 or 9; wherein:

Y is a direct bond, —$CH_2$—, or

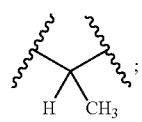

and $R^{cy}$ is phenyl, indanyl, or benzoxazolyl;

and the remaining variables are as described in embodiment no. 1.

In embodiment no. 11, the invention provides a compound of the Formula (I), wherein M is a bond or —$CH_2$—; and the remaining variables are as described in any one of embodiment nos. 1-10.

In embodiment no. 12, the invention provides a compound of the Formula (I), wherein Z is a bond and the subscript n is 4; and the remaining variables are as described in any one of embodiment nos. 1-11.

In embodiment no. 13, the invention provides a compound of the Formula (I), wherein $R^A$ is —OH or

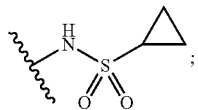 [SMILES: *NS(=O)(=O)C1CC1]

and the remaining variables are as described in any one of embodiment nos. 1-12.

In embodiment no. 14, the invention provides a compound of the Formula (I), wherein $R^{q1}$, $R^{q2}$, $R^{q3}$, $R^{q4}$ are each H; and the remaining variables are as described in any one of embodiment nos. 1-13.

In embodiment no. 15, the invention provides a compound of the Formula (I), wherein ring AH is phenyl; and the remaining variables are as described in any one of embodiment nos. 1-14.

In embodiment no. 16, the invention provides a compound of the Formula (IA),

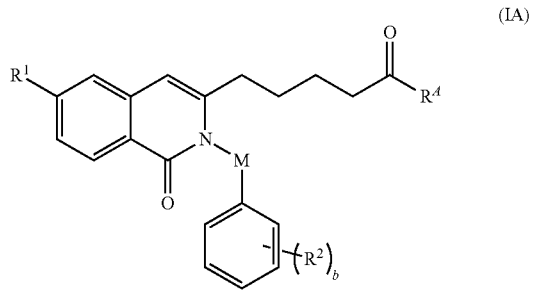

wherein
$R^A$ is —OH or

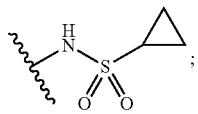 [SMILES: *NS(=O)(=O)C1CC1]

M is a bond or —CH$_2$—;
$R^1$, $R^2$, and the subscript b are as described in embodiment no. 1.

In embodiment no. 17, the invention provides a compound of the Formula (IA), wherein $R^1$ is group of the formula —C(O)N(R$^3$)(R$^4$);
$R^3$ and $R^4$ are as described in embodiment no. 3;
$R^A$ and M are as described in embodiment no. 16; and
$R^2$ and the subscript b are as described in embodiment no. 1.

In embodiment no. 18, the invention provides a compound of the Formula (IA), wherein $R^1$ is group of the formula —C(O)N(R$^3$)(R$^4$);
$R^3$ and $R^4$ are as described in embodiment no. 4;
said C$_6$-C$_{10}$ carbocyclyl of R$^{5c}$ is as described in embodiment no. 5;
$R^A$ and M are as described in embodiment no. 16; and
$R^2$ and the subscript b are as described in embodiment no. 1.

In embodiment no. 19, the invention provides a compound of the Formula (IA), wherein $R^1$ is group of the formula —C(O)N(R$^3$)(R$^4$);
$R^3$ and $R^4$ are as described in embodiment no. 7;
$R^A$ and M are as described in embodiment no. 16; and
$R^2$, $R^7$, $R^8$, and the subscripts b and u2 are as described in embodiment no. 1.

In embodiment no. 20, the invention provides a compound of the Formula (IA), wherein $R^1$ is as described in embodiment no. 9;
$R^A$ and M are as described in embodiment no. 16; and
$R^2$, WY, Y and the subscript b are as described in embodiment no. 1.

In embodiment no. 21, the invention provides a compound of the Formula (IA), wherein the subscript b is 0, 1, or 2.

In embodiment no. 22, the invention provides a compound selected from the group consisting of:
5-(2-benzyl-6-((1-(4-fluorophenyl)ethyl)carbamoyl)-1-oxo-1,2-dihydroisoquinolin-3-yl)pentanoic acid;
5-(2-(4-fluorobenzyl)-6-((1-(4-fluorophenyl)ethyl)carbamoyl)-1-oxo-1,2-dihydroisoquinolin-3-yl)pentanoic acid;
2-(2-(4-fluorophenyl)-6-((1-(4-fluorophenyl)ethyl)carbamoyl)-1-oxo-1,2-dihydroisoquinolin-3-yl)acetic acid;
5-(2-(4-fluorophenyl)-1-oxo-6-((1,2,3,4-tetrahydronaphthalen-1-yl)carbamoyl)-1,2-dihydroisoquinolin-3-yl)pentanoic acid;
5-(6-((6-fluoro-1,2,3,4-tetrahydronaphthalen-1-yl)carbamoyl)-2-(4-fluorophenyl)-1-oxo-1,2-dihydroisoquinolin-3-yl)pentanoic acid;
5-(2-(4-fluorophenyl)-1-oxo-6-((2-oxo-1,2,3,4-tetrahydroquinolin-4-yl)carbamoyl)-1,2-dihydroisoquinolin-3-yl)pentanoic acid;
5-(2-(4-fluorophenyl)-6-((1-(4-fluorophenyl)ethyl)carbamoyl)-1-oxo-1,2-dihydroisoquinolin-3-yl)pentanoic acid;
5-(6-((1-(4-fluorophenyl)ethyl)carbamoyl)-2-(4-methoxyphenyl)-1-oxo-1,2-dihydroisoquinolin-3-yl)pentanoic acid;
5-(2-(4-cyanophenyl)-6-((1-(4-fluorophenyl)ethyl)carbamoyl)-1-oxo-1,2-dihydroisoquinolin-3-yl)pentanoic acid;
5-(6-((1-(4-fluorophenyl)ethyl)carbamoyl)-2-(3-methoxyphenyl)-1-oxo-1,2-dihydroisoquinolin-3-yl)pentanoic acid;
5-(6-((1-(4-fluorophenyl)ethyl)carbamoyl)-2-(2-methoxyphenyl)-1-oxo-1,2-dihydroisoquinolin-3-yl)pentanoic acid;
5-(2-(4-fluorophenyl)-6-(4-(4-fluorophenyl)-2-methylpiperazine-1-carbonyl)-1-oxo-1,2-dihydroisoquinolin-3-yl)pentanoic acid;
5-(2-(4-fluorophenyl)-6-(2-methyl-4-phenylpiperazine-1-carbonyl)-1-oxo-1,2-dihydroisoquinolin-3-yl)pentanoic acid;
5-(6-(5-(4-fluorobenzyl)isoxazol-3-yl)-2-(4-fluorophenyl)-1-oxo-1,2-dihydroisoquinolin-3-yl)pentanoic acid;
5-(4-chloro-6-(5-(6-fluorobenzo[d]oxazol-2-yl)-5-methyl-4,5-dihydroisoxazol-3-yl)-2-(4-fluorophenyl)-1-oxo-1,2-dihydroisoquinolin-3-yl)pentanoic acid;
5-(6-(5-(6-fluorobenzo[d]oxazol-2-yl)-5-methyl-4,5-dihydroisoxazol-3-yl)-2-(4-fluorophenyl)-1-oxo-1,2-dihydroisoquinolin-3-yl)pentanoic acid;
5-(6-(5-(2,3-dihydro-1H-inden-2-yl)-1,2,4-oxadiazol-3-yl)-2-(4-fluorophenyl)-1-oxo-1,2-dihydroisoquinolin-3-yl)pentanoic acid;
5-(6-(5-(4-fluorobenzyl)-1,2,4-oxadiazol-3-yl)-2-(4-fluorophenyl)-1-oxo-1,2-dihydroisoquinolin-3-yl)pentanoic acid;

5-(2-(4-fluorophenyl)-6-(5-(1-(4-fluorophenyl)ethyl)-1,2,4-oxadiazol-3-yl)-1-oxo-1,2-dihydroisoquinolin-3-yl)pentanoic acid;
5-(2-(4-fluorophenyl)-1-oxo-6-(5-(4-(trifluoromethyl)phenyl)-1,2,4-oxadiazol-3-yl)-1,2-dihydroisoquinolin-3-yl)pentanoic acid;
3-(5-(cyclopropanesulfonamido)-5-oxopentyl)-N-(6-fluoro-1,2,3,4-tetrahydronaphthalen-1-yl)-2-(4-fluorophenyl)-1-oxo-1,2-dihydroisoquinoline-6-carboxamide;
3-(5-(cyclopropanesulfonamido)-5-oxopentyl)-2-(4-fluorophenyl)-N-(1-(4-fluorophenyl)ethyl)-1-oxo-1,2-dihydroisoquinoline-6-carboxamide;
N-(cyclopropylsulfonyl)-5-(2-(4-fluorophenyl)-6-(4-(4-fluorophenyl)-2-methylpiperazine-1-carbonyl)-1-oxo-1,2-dihydroisoquinolin-3-yl)pentanamide;
N-(cyclopropylsulfonyl)-5-(2-(4-fluorophenyl)-6-(2-methyl-4-phenylpiperazine-1-carbonyl)-1-oxo-1,2-dihydroisoquinolin-3-yl)pentanamide;
N-(cyclopropylsulfonyl)-5-(6-(5-(4-fluorobenzyl)isoxazol-3-yl)-2-(4-fluorophenyl)-1-oxo-1,2-dihydroisoquinolin-3-yl)pentanamide;
N-(cyclopropylsulfonyl)-5-(6-(5-(4-fluorobenzyl)-1,2,4-oxadiazol-3-yl)-2-(4-fluorophenyl)-1-oxo-1,2-dihydroisoquinolin-3-yl)pentanamide;
or a pharmaceutically acceptable salt thereof In embodiment no. 23, the invention provides a compound selected from the group consisting of:
(R)-5-(2-benzyl-6-((1-(4-fluorophenyl)ethyl)carbamoyl)-1-oxo-1,2-dihydroisoquinolin-3-yl)pentanoic acid;
(R)-5-(2-(4-fluorobenzyl)-6-((1-(4-fluorophenyl)ethyl)carbamoyl)-1-oxo-1,2-dihydroisoquinolin-3-yl)pentanoic acid;
(R)-2-(2-(4-fluorophenyl)-6-((1-(4-fluorophenyl)ethyl)carbamoyl)-1-oxo-1,2-dihydroisoquinolin-3-yl)acetic acid;
(R)-5-(2-(4-fluorophenyl)-1-oxo-6-((1,2,3,4-tetrahydronaphthalen-1-yl)carbamoyl)-1,2-dihydroisoquinolin-3-yl)pentanoic acid;
(R)-5-(6-((6-fluoro-1,2,3,4-tetrahydronaphthalen-1-yl)carbamoyl)-2-(4-fluorophenyl)-1-oxo-1,2-dihydroisoquinolin-3-yl)pentanoic acid;
5-(2-(4-fluorophenyl)-1-oxo-6-((2-oxo-1,2,3,4-tetrahydroquinolin-4-yl)carbamoyl)-1,2-dihydroisoquinolin-3-yl)pentanoic acid;
(R)-5-(2-(4-fluorophenyl)-6-((1-(4-fluorophenyl)ethyl)carbamoyl)-1-oxo-1,2-dihydroisoquinolin-3-yl)pentanoic acid;
(R)-5-(6-((1-(4-fluorophenyl)ethyl)carbamoyl)-2-(4-methoxyphenyl)-1-oxo-1,2-dihydroisoquinolin-3-yl)pentanoic acid;
(R)-5-(2-(4-cyanophenyl)-6-((1-(4-fluorophenyl)ethyl)carbamoyl)-1-oxo-1,2-dihydroisoquinolin-3-yl)pentanoic acid;
(R)-5-(6-(((1-(4-fluorophenyl)ethyl)carbamoyl)-2-(3-methoxyphenyl)-1-oxo-1,2-dihydroisoquinolin-3-yl)pentanoic acid;
(R)-5-(6-((1-(4-fluorophenyl)ethyl)carbamoyl)-2-(2-methoxyphenyl)-1-oxo-1,2-dihydroisoquinolin-3-yl)pentanoic acid;
(R)-5-(2-(4-fluorophenyl)-6-(4-(4-fluorophenyl)-2-methylpiperazine-1-carbonyl)-1-oxo-1,2-dihydroisoquinolin-3-yl)pentanoic acid;
(R)-5-(2-(4-fluorophenyl)-6-(2-methyl-4-phenylpiperazine-1-carbonyl)-1-oxo-1,2-dihydroisoquinolin-3-yl)pentanoic acid;
5-(6-(5-(4-fluorobenzyl)isoxazol-3-yl)-2-(4-fluorophenyl)-1-oxo-1,2-dihydroisoquinolin-3-yl)pentanoic acid;
5-(4-chloro-6-(5-(6-fluorobenzo[d]oxazol-2-yl)-5-methyl-4,5-dihydroisoxazol-3-yl)-2-(4-fluorophenyl)-1-oxo-1,2-dihydroisoquinolin-3-yl)pentanoic acid;
5-(6-(5-(6-fluorobenzo[d]oxazol-2-yl)-5-methyl-4,5-dihydroisoxazol-3-yl)-2-(4-fluorophenyl)-1-oxo-1,2-dihydroisoquinolin-3-yl)pentanoic acid;
5-(6-(5-(2,3-dihydro-1H-inden-2-yl)-1,2,4-oxadiazol-3-yl)-2-(4-fluorophenyl)-1-oxo-1,2-dihydroisoquinolin-3-yl)pentanoic acid;
5-(6-(5-(4-fluorobenzyl)-1,2,4-oxadiazol-3-yl)-2-(4-fluorophenyl)-1-oxo-1,2-dihydroisoquinolin-3-yl)pentanoic acid;
5-(2-(4-fluorophenyl)-6-(5-(1-(4-fluorophenyl)ethyl)-1,2,4-oxadiazol-3-yl)-1-oxo-1,2-dihydroisoquinolin-3-yl)pentanoic acid;
5-(2-(4-fluorophenyl)-1-oxo-6-(5-(4-(trifluoromethyl)phenyl)-1,2,4-oxadiazol-3-yl)-1,2-dihydroisoquinolin-3-yl)pentanoic acid;
(R)-3-(5-(cyclopropanesulfonamido)-5-oxopentyl)-N-(6-fluoro-1,2,3,4-tetrahydronaphthalen-1-yl)-2-(4-fluorophenyl)-1-oxo-1,2-dihydroisoquinoline-6-carboxamide;
(R)-3-(5-(cyclopropanesulfonamido)-5-oxopentyl)-2-(4-fluorophenyl)-N-(1-(4-fluorophenyl)ethyl)-1-oxo-1,2-dihydroisoquinoline-6-carboxamide;
(R)—N-(cyclopropylsulfonyl)-5-(2-(4-fluorophenyl)-6-(4-(4-fluorophenyl)-2-methylpiperazine-1-carbonyl)-1-oxo-1,2-dihydroisoquinolin-3-yl)pentanamide;
(R)—N-(cyclopropylsulfonyl)-5-(2-(4-fluorophenyl)-6-(2-methyl-4-phenylpiperazine-1-carbonyl)-1-oxo-1,2-dihydroisoquinolin-3-yl)pentanamide;
N-(cyclopropylsulfonyl)-5-(6-(5-(4-fluorobenzyl)isoxazol-3-yl)-2-(4-fluorophenyl)-1-oxo-1,2-dihydroisoquinolin-3-yl)pentanamide;
N-(cyclopropylsulfonyl)-5-(6-(5-(4-fluorobenzyl)-1,2,4-oxadiazol-3-yl)-2-(4-fluorophenyl)-1-oxo-1,2-dihydroisoquinolin-3-yl)pentanamide;
or a pharmaceutically acceptable salt thereof.

In embodiment no. 24, the invention provides a compound selected from the group consisting of:
5-(2-(4-fluorophenyl)-6-((1-(4-fluorophenyl)ethyl)carbamoyl)-1-oxo-1,2-dihydroisoquinolin-3-yl)pentanoic acid;
5-(6-((6-fluoro-1,2,3,4-tetrahydronaphthalen-1-yl)carbamoyl)-2-(4-fluorophenyl)-1-oxo-1,2-dihydroisoquinolin-3-yl)pentanoic acid;
3-(5-(cyclopropanesulfonamido)-5-oxopentyl)-N-(6-fluoro-1,2,3,4-tetrahydronaphthalen-1-yl)-2-(4-fluorophenyl)-1-oxo-1,2-dihydroisoquinoline-6-carboxamide;
5-(2-(4-fluorophenyl)-6-(2-methyl-4-phenylpiperazine-1-carbonyl)-1-oxo-1,2-dihydroisoquinolin-3-yl)pentanoic acid;
5-(6-(5-(4-fluorobenzyl)isoxazol-3-yl)-2-(4-fluorophenyl)-1-oxo-1,2-dihydroisoquinolin-3-yl)pentanoic acid;
5-(6-(5-(4-fluorobenzyl)-1,2,4-oxadiazol-3-yl)-2-(4-fluorophenyl)-1-oxo-1,2-dihydroisoquinolin-3-yl)pentanoic acid; and
N-(cyclopropylsulfonyl)-5-(6-(5-(4-fluorobenzyl)isoxazol-3-yl)-2-(4-fluorophenyl)-1-oxo-1,2-dihydroisoquinolin-3-yl)pentanamide;
or a pharmaceutically acceptable salt thereof.

The invention also provides a compound of Formula (I) or a pharmaceutically acceptable salt thereof in purified form.

Compositions and Administration

This invention is also directed to pharmaceutical compositions which comprise a therapeutically effective amount of the compound of Formula (I), or a pharmaceutically acceptable salt of said compound and a pharmaceutically acceptable carrier.

A preferred dosage is about 0.001 to 100 mg/kg of body weight/day of the compound of Formula (I). An especially preferred dosage is about 0.01 to 10 mg/kg of body weight/day of a compound of Formula (I), or a pharmaceutically acceptable salt of said compound.

The term "pharmaceutical composition" is also intended to encompass both the bulk composition and individual dosage units comprised of more than one (e.g., two) pharmaceutically active agents such as, for example, a compound of the present invention and an additional therapeutic agent selected from the lists of the additional agents described herein below, along with any pharmaceutically inactive excipients. The bulk composition and each individual dosage unit can contain fixed amounts of the aforesaid "more than one pharmaceutically active agents". The bulk composition is material that has not yet been formed into individual dosage units. An illustrative dosage unit is an oral dosage unit such as tablets, pills and the like. Similarly, the herein-described method of treating a patient by administering a pharmaceutical composition of the present invention is also intended to encompass the administration of the afore-said bulk composition and individual dosage units.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *Remington's Pharmaceutical Sciences*, 18$^{th}$ Edition, (1990), Mack Publishing Co., Easton, Pa.

Liquid form preparations include solutions, suspensions and emulsions. Examples of materials useful for forming such liquid form preparations include water or water-propylene glycol solutions for parenteral injection, or sweeteners and opacifiers for oral solutions, suspensions and emulsions. Liquid form preparations may also include solutions or suspensions for intranasal administration.

Aerosol preparations suitable for inhalation may include solutions and solids in powder form, which may be in combination with a pharmaceutically acceptable carrier, such as an inert compressed gas, e.g., nitrogen.

Also included are solid form preparations that are intended to be converted, shortly before use, to liquid form preparations for either oral or parenteral administration. Such liquid forms include solutions, suspensions and emulsions.

The compounds of the invention can also be deliverable transdermally. The transdermal compositions can take the form of creams, lotions, aerosols and/or emulsions and can be included in a transdermal patch of the matrix or reservoir type as are conventional in the art for this purpose.

The compounds of this invention may also be delivered subcutaneously.

Preferably the compound is administered orally.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 0.001 mg to about 100 mg per kg body weight of a mammal, preferably from about 0.01 mg to about 10 mg per kg. The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The compositions of the invention can further comprise one or more additional therapeutic agents, as discussed in further detail below. Accordingly, in one embodiment, the present invention provides compositions comprising: (i) a compound of Formula (I) or a pharmaceutically acceptable salt thereof; (ii) one or more additional therapeutic agents, that are not compounds of Formula (I); and (iii) a pharmaceutically acceptable carrier, wherein the amounts in the composition are together effective to treat one of the disease or conditions discussed above.

Uses of the Compounds

The compounds of Formula (I) bind to $CRTH_2$ and, therefore, are useful in characterizing tissues containing $CRTH_2$, and in identifying further compounds which bind to $CRTH_2$. The general value of the compounds of the invention in binding the $CRTH_2$ receptor can be determined, for example, using the radioligand binding assay described below in the Examples section.

The compounds of Formula (I) can also be useful as modulators of $CRTH_2$ receptor function. In some embodiments, compounds of Formula (I) are antagonists of the $CRTH_2$ receptor. The general value of the compounds of the invention in antagonizing $CRTH_2$ receptor function can be determined, for example, using the chemiluminescent-based cAMP assay, the β-Arrestin assay, or the eosinophil shape change assay described below in the Examples section.

While not being bound by any specific theory, Applicants believe that the compounds of Formula (I) are useful in treating the symptoms of diseases or conditions associated with uncontrolled or inappropriate stimulation of $CRTH_2$ function because of their ability to antagonize the $CRTH_2$ receptor. Accordingly, in one embodiment, the invention provides a method for treating a disease or conditions associated with uncontrolled or inappropriate stimulation of $CRTH_2$ function, comprising administering a therapeutically effective amount of a compound of Formula (I) to a patient in need of such treatment.

Diseases or conditions associated with uncontrolled or inappropriate stimulation of $CRTH_2$ function include (but are not limited to) asthma (including allergic asthma), congestion, allergic rhinitis, atopic dermatitis, chronic obstructive pulmonary disease ("COPD"), dermatitis, inflammatory bowel disease, rheumatoid arthritis, allergic nephritis, conjunctivitis, bronchial asthma, fold allergy, systemic mast cell disorder, anaphylactic shock, urticaria, eczema, itching, inflammation, ischemia-reperfusion injury, cerebrovascular disorders, pleuritis, ulcerative colitis, eosinophil-related diseases, such as Churg-Strauss syndrome and sinusitis, and basophile-related diseases, such as basophilic leukemia and basophilic leukocytosis, in humans and other mammals. Examples of cerebrovascular disorders include stroke.

In certain embodiments, the present invention provides a method for treating asthma, congestion, allergic rhinitis or COPD which comprises administering a therapeutically effective dose of a compound of Formula (I) or a pharmaceutically acceptable salt thereof to a patient in need of such treatment. In a specific embodiment, the disease or condition being treated is asthma. In another embodiment, the disease or condition being treated is COPD.

In addition, compounds of the Formula (I) which act as $CRTH_2$ receptor antagonists can inhibit prostanoid-induced smooth muscle contraction by antagonizing contractile prostanoids or mimicking relaxing prostanoids and hence may be used in the treatment of dysmenorrhea, premature labor and eosinophil related disorders.

In another embodiment, the present invention provides a compound of Formula (I) or a pharmaceutically acceptable salt thereof for use in the manufacture of a medicament for treating a disease or condition selected from the group consisting of asthma, congestion, allergic rhinitis, atopic dermatitis, COPD, dermatitis, inflammatory bowel disease, rheumatoid arthritis, allergic nephritis, conjunctivitis, bronchial asthma, food allergy, systemic mast cell disorder, anaphylactic shock, urticaria, eczema, itching, inflammation, ischemia-reperfusion injury, cerebrovascular disorders, pleuritis, ulcerative colitis, eosinophil-related diseases, such as Churg-Strauss syndrome and sinusitis, and basophile-related diseases, such as basophilic leukemia and basophilic leukocytosis.

In another embodiment, the present invention provides a compound of Formula (I) or a pharmaceutically acceptable salt thereof for use in treating a disease or condition from the group consisting of asthma, congestion, allergic rhinitis, atopic dermatitis, COPD, dermatitis, inflammatory bowel disease, rheumatoid arthritis, allergic nephritis, conjunctivitis, bronchial asthma, food allergy, systemic mast cell disorder, anaphylactic shock, urticaria, eczema, itching, inflammation, ischemia-reperfusion injury, cerebrovascular disorders, pleuritis, ulcerative colitis, eosinophil-related diseases, such as Churg-Strauss syndrome and sinusitis, and basophile-related diseases, such as basophilic leukemia and basophilic leukocytosis.

Combination Therapy

The compounds of Formula (I) or their pharmaceutically acceptable salts may be used in combination, either in a single formulation or co-administered as separate formulations with at least one additional therapeutic agent to treat or prevent the diseases and conditions described herein. These additional therapeutic agents include, but are not limited to: (1) a DP receptor antagonist, such as S-5751 and laropiprant; (2) a corticosteroid, such as triamcinolone acetonide, budesonide, beclomethasone, fluticasone and mometasone; (3) a β2-adrenergic agonist, such as salmeterol, formoterol, arformoterol, terbutaline, metaproterenol, albuterol and the like; (4) a leukotriene modifier, including a leukotriene receptor antagonist, such as montelukast, zafirlukast, pranlukast, or a lipooxygenase inhibitor including 5-lipooxygenase inhibitors and FLAP (5-lipooxygenase activating protein) inhibitors, such as zileuton; (5) an antihistamine such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (6) a decongestant, including phenylephrine, phenylpropanolamine, pseudoephedrine, oxymetazoline, ephinephrine, naphazoline, xylometazoline, propylhexedrine, or levo-desoxyephedrine; (7) an antiitussive, including codeine, hydrocodone, caramiphen, carbetapentane, or dextramethorphan; (8) another prostaglandin ligand, including prostaglandin F agonist such as latanoprost; misoprostol, enprostil, rioprostil, ornoprostol or rosaprostol; (9) a diuretic; (10) non-steroidal antiinflammatory agents (NSAIDs), such as propionic acid derivatives (alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (11) cyclooxygenase-2 (COX-2) inhibitors, such as celecoxib and rofecoxib; (12) inhibitors of phosphodiesterase type IV (PDE-IV) e.g., Ariflo, roflumilast; (13) antagonists of the chemokine receptors, especially CCR-1, CCR-2, and CCR-3; (14) cholesterol lowering agents such as HMG-CoA reductase inhibitors (lovastatin, simvastatin and pravastatin, fluvastatin, atorvastatin, and other statins), sequestrants (cholestyramine and colestipol), nicotinic acid, fenofibric acid derivatives (gemfibrozil, clofibrat, fenofibrate and benzafibrate), and probucol; (15) anti-diabetic agents such as insulin, sulfonylureas, biguanides (metformin), α-glucosidase inhibitors (acarbose) and glitazones (troglitazone, pioglitazone, englitazone, rosiglitazone and the like); (16) preparations of interferon beta (interferon beta-la, interferon beta-1b); (17) anticholinergic agents, such as muscarinic antagonists (ipratropium bromide and tiotropium bromide), as well as selective muscarinic M3 antagonists; (18) steroids such as beclomethasone, methylprednisolone, betamethasone, prednisone, dexamethasone, and hydrocortisone; (19) triptans commonly used for the treatment of migraine such as sumitriptan and rizatriptan; (20) alendronate and other treatments for osteoporosis; (21) other compounds such as 5-aminosalicylic acid and prodrugs thereof, antimetabolites such as azathioprine and 6-mercaptopurine, cytotoxic cancer chemotherapeutic agents, bradykinin (BK2) antagonists such as FK-3657, TP receptor antagonists such as seratrodast, neurokinin antagonists (NK1/NK2), VLA-4 antagonists, such as those described in U.S. Pat. No. 5,510,332, WO97/03094, WO97/02289, WO96/40781, WO96/22966, WO96/20216, WO96/01644, WO96/06108, WO95/15973 and WO96/31206. In addition, the invention encompasses a method of treating prostaglandin D2 mediated diseases comprising: administration to a patient in need of such treatment a non-toxic therapeutically effective amount of a compound of Formula (I), optionally co-administered with one or more of such ingredients as listed immediately above.

When administering a combination therapy to a patient in need of such administration, the therapeutic agents in the combination, or a pharmaceutical composition or compositions comprising the therapeutic agents, may be administered in any order such as, for example, sequentially, concurrently, together, simultaneously and the like.

In one embodiment, the compound of Formula (I) is administered during a time when the additional therapeutic agent(s) exert their prophylactic or therapeutic effect, or vice versa.

In another embodiment, the compound of Formula (I) and the additional therapeutic agent(s) are administered in doses commonly employed when such agents are used as monotherapy for treating the disorder.

In another embodiment, the compound of Formula (I) and the additional therapeutic agent(s) are administered in doses lower than the doses commonly employed when such agents are used as monotherapy for treating the disorder.

In one embodiment, the compound of Formula (I) and the additional therapeutic agent(s) are present in the same composition, which is suitable for oral administration.

In one embodiment, the additional therapeutic agent present in the same composition is a leukotriene receptor antagonist, such as montelukast, zafirlukast, pranlukast. In one particular embodiment the leukotriene receptor antagonist is montelukast.

The compound of Formula (I) and the additional therapeutic agent(s) can act additively or synergistically. A synergistic combination may allow the use of lower dosages of one or more agents and/or less frequent administration of one or more agents of a combination therapy. A lower dosage or less frequent administration of one or more agents may lower toxicity of the therapy without reducing the efficacy of the therapy.

The doses and dosage regimen of the additional therapeutic agent(s) used in the combination therapies of the present invention for the treatment or prevention of a disease or disorder can be determined by the attending clinician, taking into consideration the approved doses and dosage regimen in the package insert; the age, sex and general health of the patient; and the type and severity of the disease or disorder.

Another aspect of this invention is a kit comprising a therapeutically effective amount of the compound of Formula (I) or a pharmaceutically acceptable salt of said compound, optionally at least one additional therapeutic agent listed above and a pharmaceutically acceptable carrier, vehicle or diluent.

Methods of Preparing the Compounds of Formula (I)

In general, the compounds in the invention may be produced by a variety of processes known to those skilled in the art and by know, processes analogous thereto. The invention disclosed herein is exemplified by the following preparations and examples which should not be construed to limit the scope of the disclosure. Alternative mechanistic pathways and analogous structures will be apparent to those skilled in the art. The practitioner is not limited to these methods. Illustrative general synthetic methods are set out below and then specific compounds of the Formula (I) are prepared in the Examples.

Scheme 1

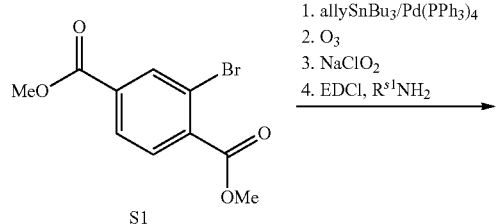

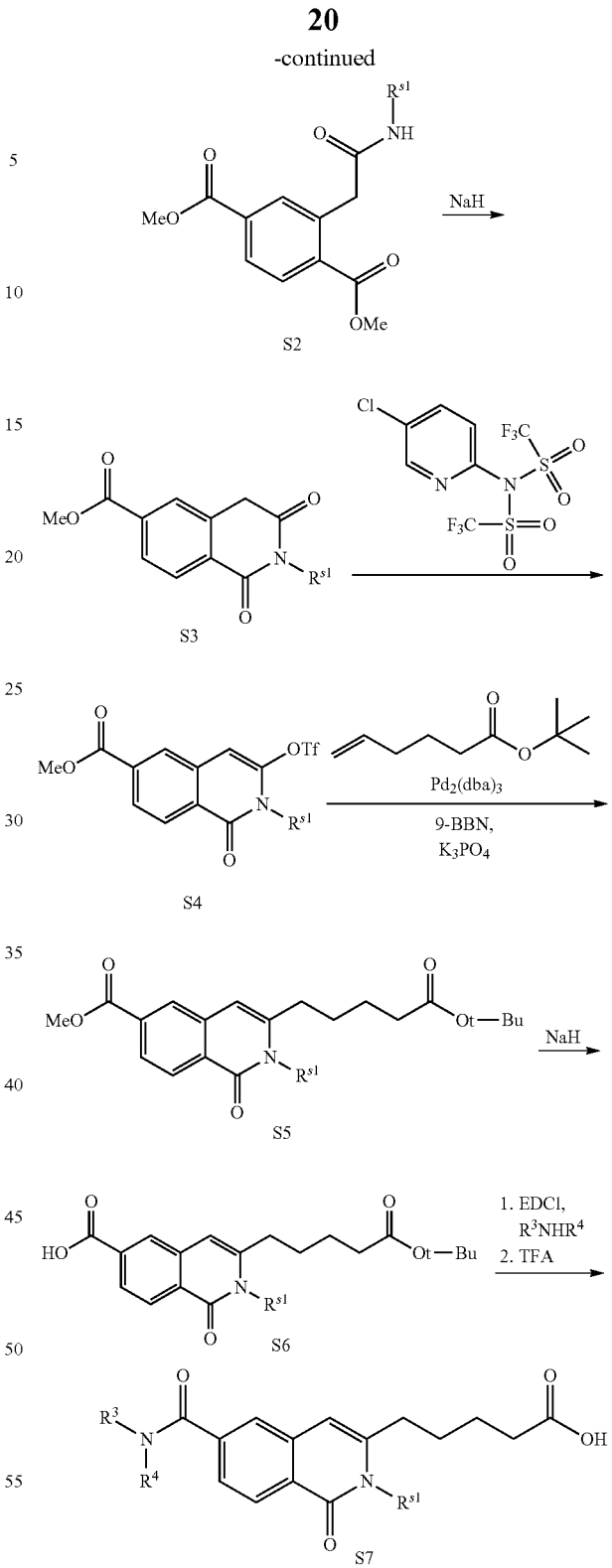

The synthesis of acid S7 (wherein —$R^{s1}$=-M-AH) starts from commercially available compound S1. A four step process can convert S1 to amide S2 which cyclizes under basic conditions to give compound S3. Triflation of S3 provides S4 which can be coupled with desired alkenes to give S5. Compound S7 can be synthesized from S5 by hydrolysis, amide coupling, and TFA deprotection.

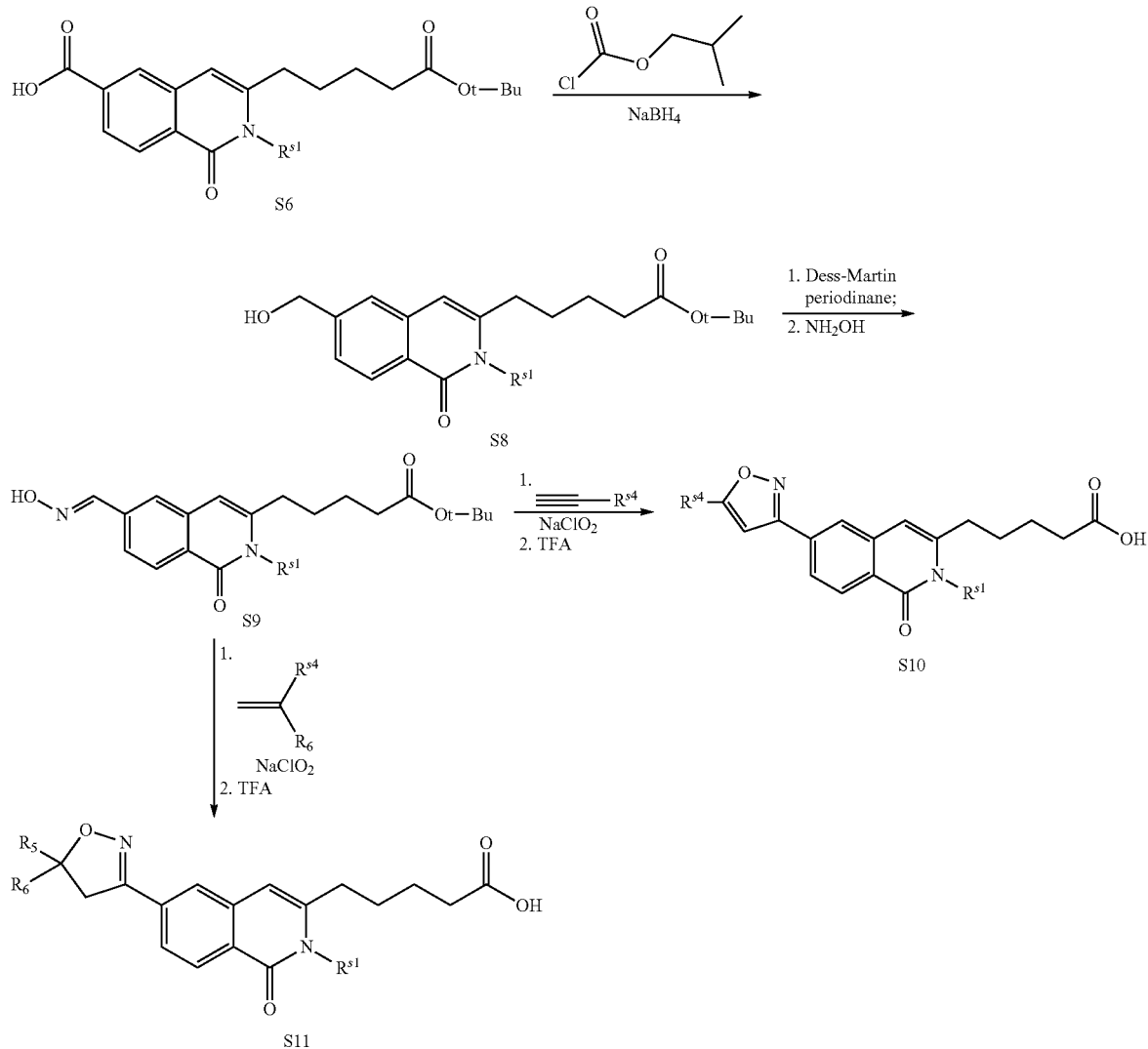

The synthesis of compounds of the invention wherein $R^1$ is a substituted isoxazole or isoxazoline ring starts from compound S6. Alcohol S8 can be obtained from S6 under reductive reaction conditions. Compound S8 is converted to oxime S9 through oxidation and treatment with hydroxylamine. Isooxazole S10 and isooxazoline S11 can be synthesized from S9 in the presence of alkyne and alkene (wherein —$R^{s4}$ is —Y—$R^{cy}$), respectively, then acid deprotection.

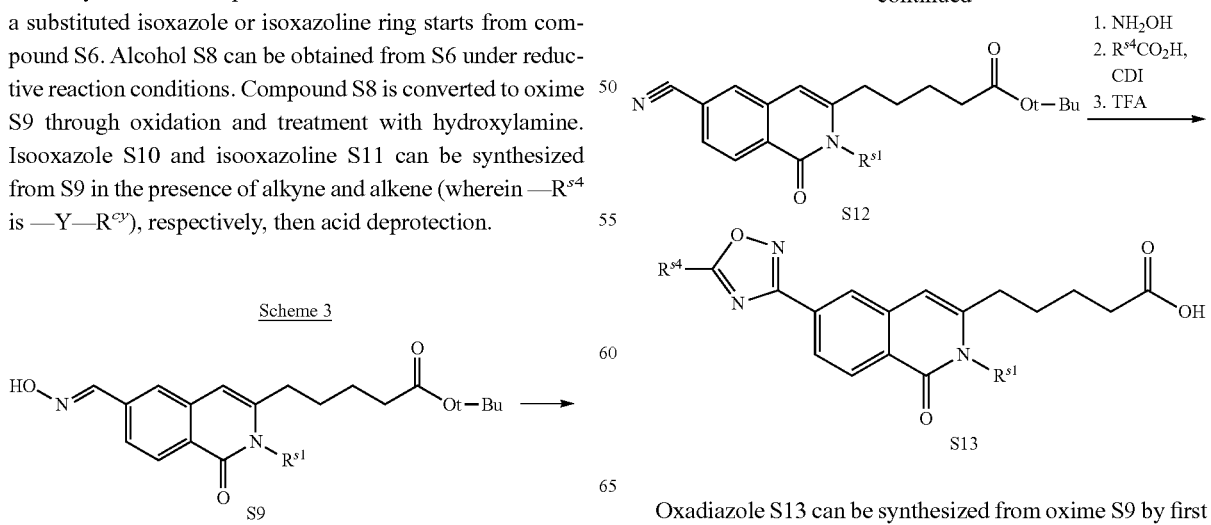

Oxadiazole S13 can be synthesized from oxime S9 by first converting it to nitrile 512. Compound S12 is transformed to final compound S13 in three steps through imidate formation, CDI coupling with acids, and deprotection with TFA.

Scheme 4

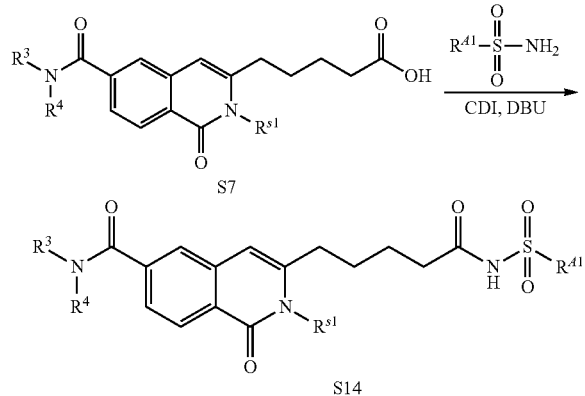

Acids 7 can be converted to its bioisosteres S14 in the presence of sulfamide, CDI and DBU.

Scheme 5

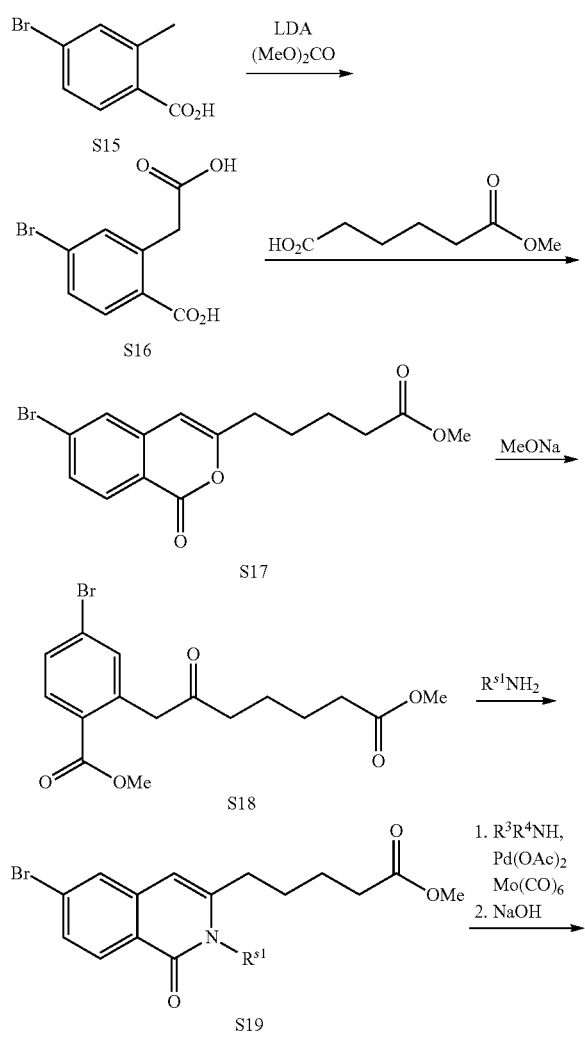

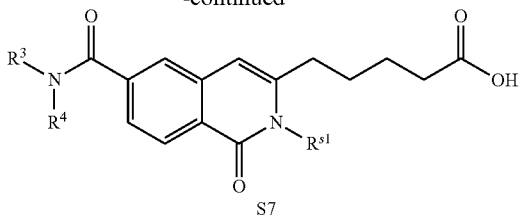

Acid S7 can be synthesized by a second route. Compound S16 is synthesized from S15 in the presence of LDA and methylcarbamate. Condensation of S16 with adipic acid monomethyl ester gives lactone S17 which can be converted to lactam S19 by ring opening with sodium methoxide and condensation with amines Final compound S7 is obtained from S19 by the aminocarbonation reaction followed with acid deprotection.

One skilled in the art will recognize that one route will be optimized depending on the choice of appendage substituents. Additionally, one skilled in the art will recognize that in some cases the order of steps has to be controlled to avoid functional group incompatibility.

The prepared compounds may be analyzed for their composition and purity as well as characterized by standard analytical techniques such as, for example, elemental analysis, NMR, mass spectroscopy and IR spectra.

One skilled in the art will recognize that reagents and solvents actually used may be selected from several reagents and solvents well known in the art to be effective equivalents. Hence, when a specific solvent or reagent is mentioned, it is meant to be an illustrative example of the conditions desirable for that particular reaction scheme or for the preparation described below.

Where NMR data are presented in the preparations below, $^1$H spectra were obtained on either a Varian VXR-400 (400 MHz, 1H), Varian Gemini-300 (300 MHz), Varian Mercury VX-400 (400 MHz), Bruker-Biospin AV-500 (500 MHz) or Bruker Avance DRX-500 (500 MHz), and chemical shifts are reported as ppm with number of protons and multiplicities indicated parenthetically. Where LC/MS data are presented, analyses was performed using a 1200 series Agilent 6140 Quadrupole LCMS with a 1.8 μM Zorbax SB-C18 column (10-95% of MeCN—H$_2$O with 0.1% TFA over 2.7 min, 1 mL/min) or with an Applied Biosystems API-150 mass spectrometer and Gemini C18 column (50×4.6 mm, 10-95% CH$_3$CN—H$_2$O with 0.05% TFA over 5 min, 1 mL/min)

Preparative chiral HPLC separations were generally carried out using supercritical fluid chromatography by eluting a chiral column such as OJ-H, (4.6×250 mm, Chiral Technologies, Inc., West Chester, Pa.) with a mobile phase of isopropanol and supercritical CO$_2$.

The following solvents, reagents, protecting groups, moieties, and other designations may be referred to by their abbreviations in parenthesis:

Me=methyl; Et=ethyl; Pr=propyl; iPr—isopropyl; Bu=butyl; t-Bu32 tert-butyl; Ph=phenyl, and Ac=acetyl
μl=microliters
EtOAc=ethyl acetate
AcOH or HOAc=acetic acid
aq=aqueous
Ar=aryl
atm=atmosphere
9-BBN=9-borabicyclo[3.3.1]nonane
Bn=benzyl
Boc or BOC=tert-butoxycarbonyl Bz=benzoyl
Boc=tert-butoxycarbonyl
cat=catalyst or catalytic
Cbz or CBZ=benyzloxycarbonyl
CDI=1,1'-carbonyldiimidazole
dba=dibenzylideneacetone
DBU=1,8-Diaza-7-bicyclo[5.4.0]undecene
DCM=dichloromethane
DCE=dichloroethane
DMAP=4-dimethylaminopyridine
DIBAL=diisobutylaluminum hydride
DIPEA or Hünig's Base=N,N-diisopropylethylamine
DME=1,2-dimethoxyethane
DMF=dimethylformamide
DMS=dimethylsulfide
DMSO=dimethyl sulfoxide
EDC or EDCI=1-(3-dimethylaminopropyl)-3-ethylcarbodiimide
ee=enantiomeric excess
EDTA=ethylenediaminetetraacetic acid
Et$_2$O=diethyl ether
g=grams
h=hour
HMDS=1,1,1,3,3,3-hexamethyldisilazane
HOBt=1-hydroxybenzotriazole
Im=imidazole
LAH=lithium aluminum hydride
LDA=lithium diisopropylamide
LCMS=liquid chromatography mass spectrometry
LG=leaving group
min=minute
mg=milligrams
mL=milliliters
mmol=millimoles
MeOH: methanol
MS=mass spectrometry
NBS=N-bromosuccimide
NMR=nuclear magnetic resonance spectroscopy
Obsv'd=observed
PG=protecting group
PTLC=preparative thin layer chromatography
Pyr=pyridine
RT or rt=room temperature (ambient, about 25° C.)
sat=saturated
SFC=supercritical fluid chromatography
SM=starting material
TBSCl=t-butyldimethylsilyl chloride
TBS=t-butyldimethyl silyl
TFA=trifluoroacetic acid
TFAA=trifluoroacetic anhydride
THF=tetrahydrofuran
TLC=thin layer chromatography
TMS=trimethylsilyl
Tos or Ts=p-toluenesulfonyl(tosyl)
Tot=toluene
IBMX==3-Isobutyl-1-methylxanthine
HBSS=Hank's balanced salt solution
HEPES=1-[4-(2-hydroxyethyl)-1-piperazinyl]ethane-2-sulfonic acid The compounds of this invention can be prepared through the general approach outlined in the following schemes. These schemes are being provided to illustrate the present invention. To assist one in this endeavor, the ordinary practitioner would have full knowledge of literature sources such as *Chemical Abstracts; Beilstein, Protective Groups in Organic Synthesis* 2$^{nd}$ Edition T. W. Greene, P.G.M. Wuts 1991, *Wiley and Sons; Comprehensive Organic Transformations, Advanced Organic Chemistry* etc.

These examples are being provided to further illustrate the present invention. They are for illustrative purposes only; the scope of the invention is not to be considered limited in any way thereby.

EXAMPLES

Example 1

Preparation of Compounds of the Invention where M-AH is a Benzylic Substituent

Example 1.1

(R)-5-(2-benzyl-6-((1-(4-fluorophenyl)ethyl)carbamoyl)-1-oxo-1,2-dihydroisoquinolin-3-yl)pentanoic acid Step 1:

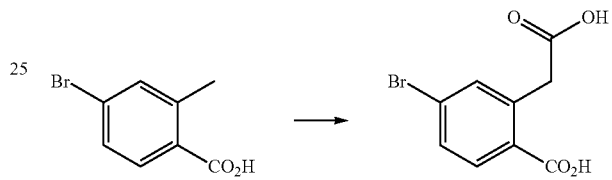

To a solution of diisopropylamine (13.26 mL, 93 mmol, 4.0 equiv.) in THF (50 mL) was slowly added n-BuLi (37.2 mL, 93 mmol, 4.0 equiv.) at −78° C. The mixture was allowed to warm to 0° C. and stirred at that temperature for 5 min. The reaction was cooled back to −78° C. and to this mixture was slowly added 4-bromo-2-methylbenzoic acid (5.0 g, 23.25 mmol) and dimethyl carbonate (3.91 mL, 46.5 mmol, 2.0 equiv.) in THF (50 mL) and the mixture was stirred at −78° C. for 5 min. The dry ice bath was removed and the reaction was allowed to stir at room temperature for 4 h. Upon completion of the reaction, the mixture was quenched by the addition of 75 mL water and allowed to stir overnight. The aqueous layer was separated from the organic layer. The aqueous layer was acidified with conc. HCl until pH 2, extracted with EtOAc (2×50 mL), dried over Na$_2$SO$_4$, filtered and evaporated to dryness to yield a white solid. The solid was recrystallized from hot EtOAc/hexanes to yield 5.65 g of 4-bromo-2-(carboxymethyl)benzoic acid as a white solid.

Step 2:

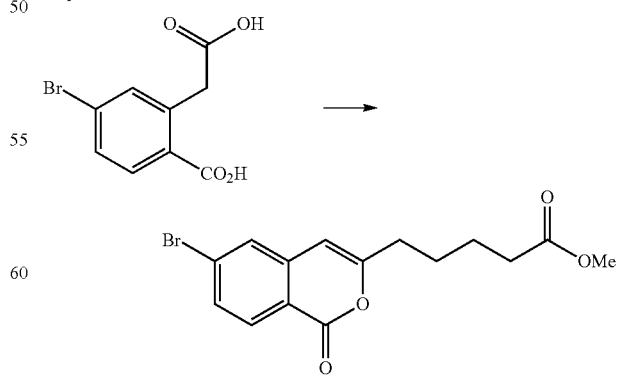

To a stirred mixture of adipic acid monomethyl ester (9.27 g, 57.9 mmol, 1.50 equiv.) in THF (50 mL) was added N,N'- carbonyldiimidazole (9.39 g, 57.9 mmol, 1.50 equiv.) and the mixture was stirred at room temperature. After stirring for 30 min, the reaction mixture was cooled to 0° C. followed by dropwise addition of 4-bromo-2-(carboxymethyl)benzoic acid (10.0 g, 38.6 mmol) in THF (25 mL). The reaction was stirred gradually from 0° C. to room temperature for 48 h. Upon completion of the reaction, 0.5 N HCl (25 mL) solution was added and extracted with EtOAc (2×25 mL). The organic layer was washed with aqueous sat. NaHCO₃, dried over Na₂SO₄, filtered and evaporated to dryness. The residue was purified by column chromatography on silica gel eluting with 0-15% EtOAc/hexanes to give 1.5 g of methyl 5-(6-bromo-1-oxo-1H-isochromen-3-yl)pentanoate as a white solid.

Step 3:

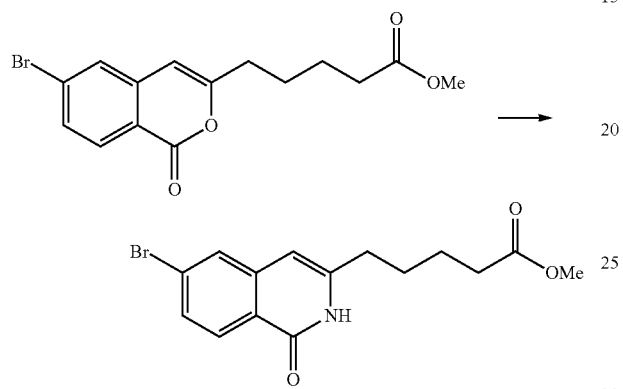

A mixture of methyl 5-(6-bromo-1-oxo-1H-isochromen-3-yl)pentanoate (1.5 g, 4.42 mmol) in 7 N ammonia in MeOH (63.2 ml, 442 mmol, 100.0 equiv.) was left standing at room temperature overnight. The mixture was concentrated, diluted with EtOAc, and added 1 N HCl until pH 4. The mixture was vigorously stirred for 10 min, extracted with EtOAc (2×20 mL), washed with brine, dried over Na₂SO₄, filtered and evaporated to dryness to yield 1.26 g of methyl 5-(6-bromo-1-oxo-1,2-dihydroisoquinolin-3-yl)pentanoate which was used as such without any further purification.

Step 4:

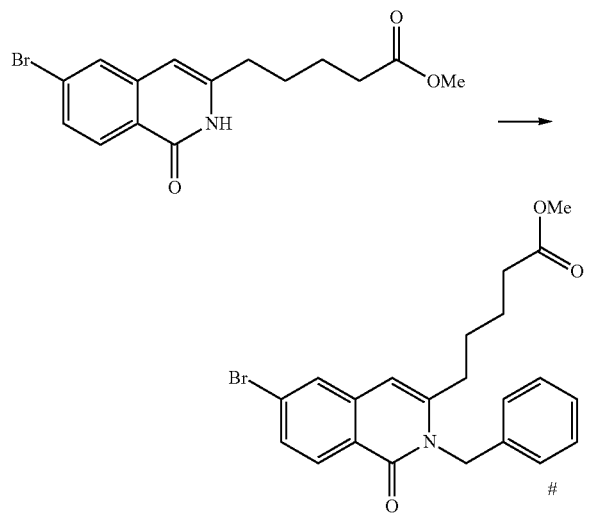

Benzyl bromide (152 mg, 0.887 mmol, 1.50 equiv.) was added to a stirred mixture of methyl 5-(6-bromo-1-oxo-1,2-dihydroisoquinolin-3-yl)pentanoate (200 mg, 0.591 mmol) and Cs₂CO₃ (289 mg, 0.887 mmol, 1.50 equiv.) in DMF (1 mL) and the mixture was stirred at room temperature overnight. Upon completion, the reaction mixture was diluted with water, extracted with EtOAc (2×5 mL), washed with brine, dried over Na₂SO₄, filtered and evaporated to dryness. The residue was purified by column chromatography on silica gel, eluting with 0-20% EtOAc/hexanes to give 147 mg of methyl 5-(2-benzyl-6-bromo-1-oxo-1,2-dihydroisoquinolin-3-yl)pentanoate as a pink solid.

Steps 5 and 6:

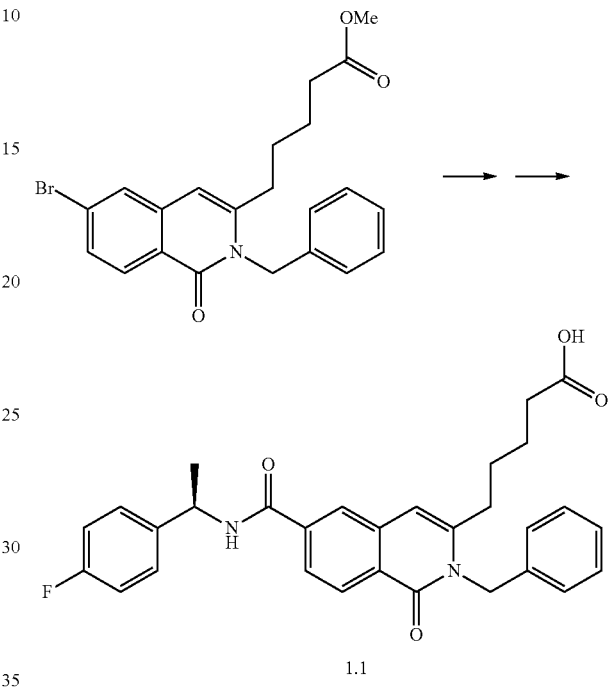

1.1

DBU (4.50 equiv.) was added to a stirred, capped mixture of methyl 5-(2-benzyl-6-bromo-1-oxo-1,2-dihydroisoquinolin-3-yl)pentanoate (1 eq), Pd(OAc)2 (0.05 equiv.), molybdenum hexacarbonyl (1.0 equiv.) and (R)-1-(4-fluorophenyl)ethylamine (1.20 equiv.) in THF (0.2 M) and the mixture was stirred at 150° C. for 30 min. in a microwave. The mixture was purified by preparative TLC [1 mm] eluting with 50% EtOAc/hexanes to afford (R)-methyl 5-(2-benzyl-6-((1-(4-fluorophenyl)ethyl)carbamoyl)-1-oxo-1,2-dihydroisoquinolin-3-yl)pentanoate.

Lithium hydroxide monohydrate (4.0 equiv.) in water (0.66 M) was added to a stirred mixture of (R)-methyl 5-(2-benzyl-6-((1-(4-fluorophenyl)ethyl)carbamoyl)-1-oxo-1,2-dihydroisoquinolin-3-yl)pentanoate (1 eq) in MeOH/THF (v/v=1/4) and the mixture was stirred at room temperature. After 2 h, the mixture was neutralized with 1 N HCl, extracted with EtOAc, dried over Na₂SO₄, filtered and evaporated to dryness. To the residue was added Et₂O and sonicated, upon which some solid precipitated. The solids were filtered, triturated with Et₂O and dried to yield (R)-5-(2-benzyl-6-((1-(4-fluorophenyl)ethyl)carbamoyl)-1-oxo-1,2-dihydroisoquinolin-3-yl)pentanoic acid. LCMS [M+H]⁺=501. ¹H NMR (CDCl₃, 500 MHz) δ ppm: 8.44 (d, 1H, J=8.5 Hz), 7.92 (br s, 1H), 7.71 (d, 1H, J=8.0 Hz), 7.40 (dd, 2H, J=5.0 Hz, J=8.5 Hz), 7.32-7.23 (m, 3H), 7.12 (d, 2H, J=7.5 Hz), 7.06 (t, 2H, J=9.0 Hz), 6.42 (s, 1H), 5.43 (br s, 2H), 5.39-5.35 (m, 1H), 2.63 (t, 2H, J=7.5 Hz), 2.37 (t, 2H, J=6.5 Hz), 1.70-1.64 (m, 4H), 1.63 (d, 3H, J=7.0 Hz).

The following compound was prepared using a similar procedure as described for Example 1.1 by substituting 4-fluorobenzyl bromide for benzyl bromide in step 4.

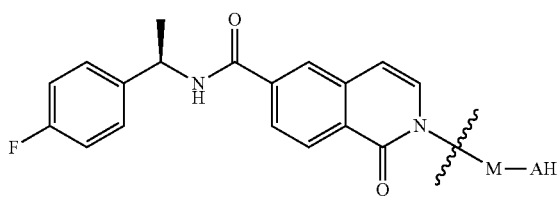

| Ex. No. Name | —M—AH | [M + H]+ Obsv'd |
|---|---|---|
| 1.2 (R)-5-(2-(4-fluorobenzyl)-6-((1-(4-fluorophenyl)ethyl)carbamoyl)-1-oxo-1,2-dihydroisoquinolin-3-yl)pentanoic acid | 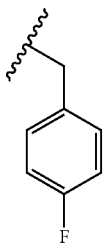 [SMILES: *Cc1ccc(F)cc1] | 519 |

Example 2

Preparation of Compounds of the Invention where Z is a Bond and the Subscript n is 1

Example 2.1

(R)-2-(2-(4-fluorophenyl)-6-((1-(4-fluorophenyl)ethyl)carbamoyl)-1-oxo-1,2-dihydroisoquinolin-3-yl) acetic acid Step 1:

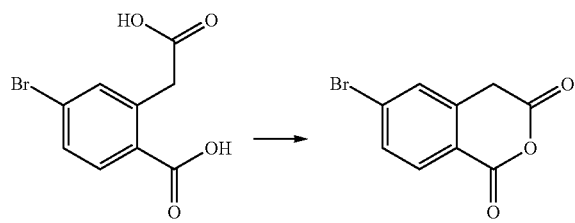

A mixture of 4-bromo-2-(carboxymethyl)benzoic acid (1.00 g, 3.86 mmol) in acetyl chloride (13.72 ml, 193 mmol, 50.0 equiv.) was stirred at 150° C. for 15 min. in a microwave. Upon completion of the reaction, the excess solvent was concentrated and dried to yield 740 mg of 6-bromoisochroman-1,3-dione as a white solid which was used as such without any further purification.

Step 2:

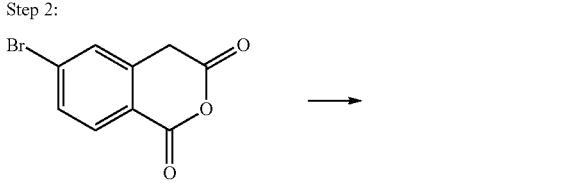

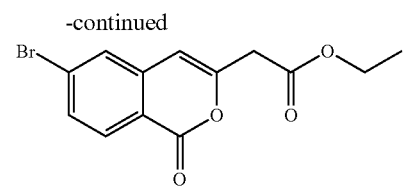

N,N'-Carbonyldiimidazole (747 mg, 4.61 mmol, 1.50 equiv.) was added to a stirred mixture of ethyl hydrogen malonate (0.543 mL, 4.61 mmol, 1.50 equiv.) in THF (15 mL) and the mixture was stirred at room temperature. After 15 min, Hunig's base (1.072 mL, 6.14 mmol, 2.00 equiv.) was added followed by dropwise addition of 6-bromoisochroman-1,3-dione (740 mg, 3.07 mmol) in THF (10 mL). Upon completion, the reaction was diluted with 0.5 N HCl (10 mL), extracted with EtOAc (2×20 mL), dried over Na$_2$SO$_4$, filtered and evaporated to dryness. The residue was purified by column chromatography on silica gel eluting with 0-15% EtOAc/hexanes to give 683 mg of ethyl 2-(6-bromo-1-oxo-1H-isochromen-3-yl)acetate as a white solid.

Step 3:

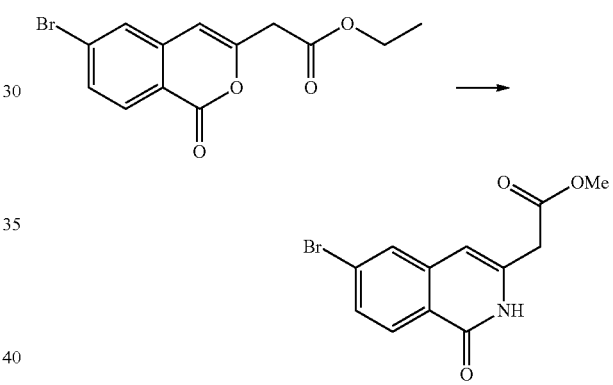

A solution of 7 N ammonia in MeOH (3.14 mL, 21.95 mmol, 10.0 equiv.) and ethyl 2-(6-bromo-1-oxo-1H-isochromen-3-yl)acetate (683 mg, 2.195 mmol) was stirred at room temperature for 1 h. Upon completion of the reaction, the excess solvent was concentrated, diluted with 1 N HCl (5 mL), and extracted with EtOAc (2×5 mL). The organic layer was dried over Na$_2$SO$_4$, filtered and evaporated to dryness. The residue was purified by column chromatography on silica gel eluting with 0-40% EtOAc/hexanes to give 250 mg of methyl 2-(6-bromo-1-oxo-1,2-dihydroisoquinolin-3-yl)acetate as a white solid.

Step 4:

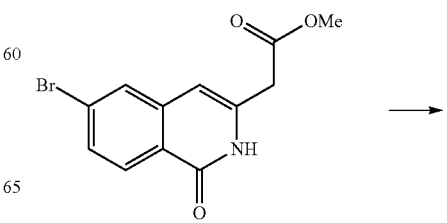

-continued

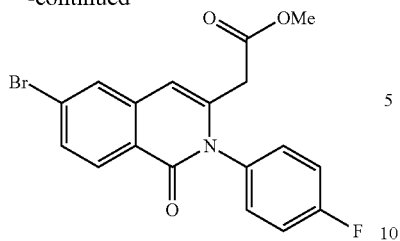

Copper (II) acetate (67.5 mg, 0.371 mmol, 1.10 equiv.) and 4-fluorophenylboronic acid (95 mg, 0.675 mmol, 2.00 equiv.) were added to a stirred mixture of methyl 2-(6-bromo-1-oxo-1,2-dihydroisoquinolin-3-yl)acetate (100 mg, 0.338 mmol) and pyridine (54.6 µl, 0.675 mmol, 2.00 equiv.) in CH$_2$Cl$_2$ (3 mL) and the mixture was stirred in air at room temperature overnight in the presence of 4 Å molecular sieves. 1 N HCl (3 mL) was added to the reaction mixture and extracted with DCM (2×5 mL), dried over Na$_2$SO$_4$, filtered and evaporated to dryness. The residue was purified by column chromatography on silica gel eluting with 0-15-20% EtOAc/hexanes to give 34 mg of methyl 2-(6-bromo-2-(4-fluorophenyl)-1-oxo-1,2-dihydroisoquinolin-3-yl)acetate as a pale yellow solid.

Steps 5 and 6:

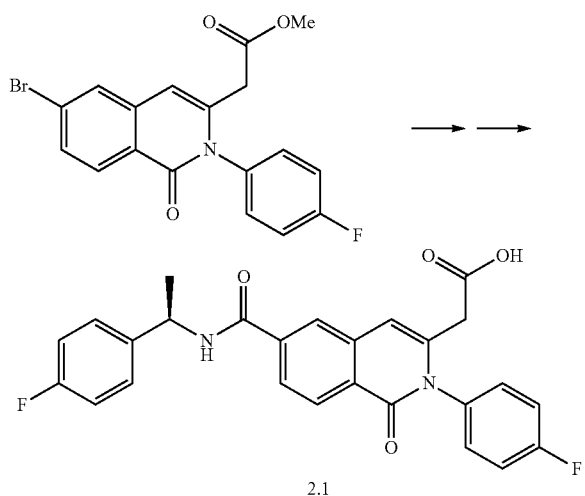

2.1

In a manner similar to that previously described for Example 1, steps 5 and 6, methyl 2-(6-bromo-2-(4-fluorophenyl)-1-oxo-1,2-dihydroisoquinolin-3-yl)acetate was aminocarbonylated with (R)-1-(4-fluorophenyl)ethylamine and hydrolyzed with LiOH to provide (R)-2-(2-(4-fluorophenyl)-6-((1-(4-fluorophenyl)ethyl)carbamoyl)-1-oxo-1,2-dihydroisoquinolin-3-yl)acetic acid. LCMS: [M+H]$^+$=463. $^1$H NMR (DMSO, 500 MHz) δ ppm: 12.49 (br s, 1H), 9.09 (d, 1H, J=8.0 Hz), 8.22 (d, 1H, J=8.0 Hz), 8.14 (s, 1H), 7.94 (d, 1H, J=8.0 Hz), 7.47 (dd, 2H, J=6.0 Hz, J=8.0 Hz), 7.38-7.31 (m, 3H), 7.17 (t, 2H, J=9.0 Hz), 6.81 (s, 1H), 5.24-5.18 (m, 1H), 3.45 (s, 2H), 1.51 (d, 3H, J=7.0 Hz).

Example 3

Preparation of Compounds Prepared According to Scheme 5

Example 3.1

(R)-5-(2-(4-fluorophenyl)-1-oxo-6-((1,2,3,4-tetrahydronaphthalen-1-yl)carbamoyl)-1,2-dihydroisoquinolin-3-yl)pentanoic acid Step 1:

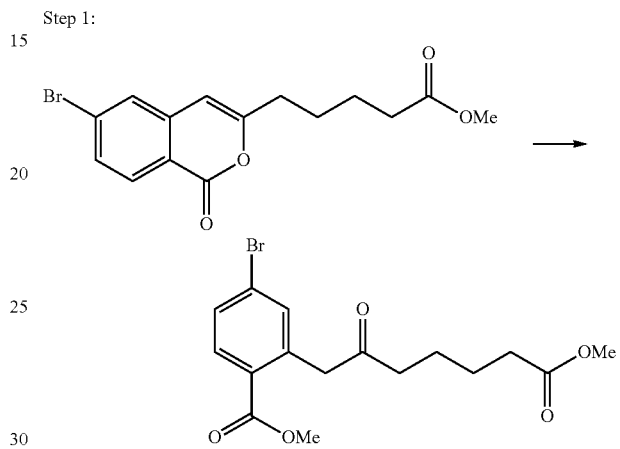

Sodium methoxide (0.222 mL, 0.973 mmol, 1.10 equiv.) was added to a stirred mixture of methyl 5-(6-bromo-1-oxo-1H-isochromen-3-yl)pentanoate (300 mg, 0.884 mmol) in MeOH (2 mL) and the reaction was stirred at 50° C. for 90 min. Upon cooling to room temperature, the mixture was concentrated and dried to yield 328 mg of a mixture of starting material and methyl 4-bromo-2-(7-methoxy-2,7-dioxoheptyl)benzoate as a brown gum. The residue was used as such for the next step without any further purification.

Step 2:

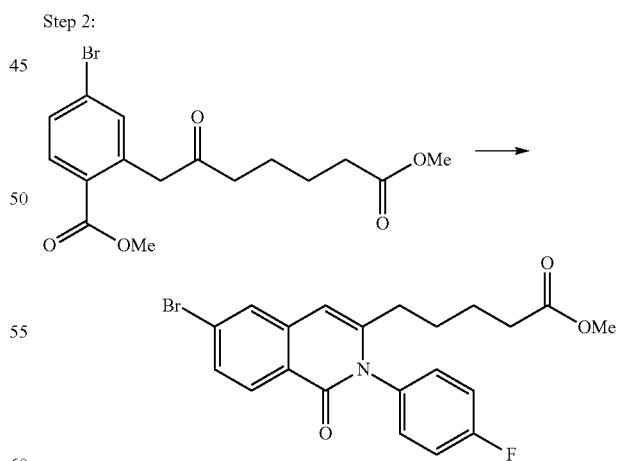

4-Fluoroaniline (98 mg, 0.884 mmol, 1.0 equiv.) was added to a stirred mixture of methyl 4-bromo-2-(7-methoxy-2,7-dioxoheptyl)benzoate (328 mg, 0.884 mmol) in acetic acid (1 mL) and the mixture was stirred at 100° C. for 90 min. After cooling to room temperature, the excess solvent was concentrated, diluted with water and extracted with EtOAc (2×5 mL). The organic layer was dried over Na₂SO₄, filtered and evaporated to dryness. The residue was purified by column chromatography on silica gel eluting with 0-10% EtOAc/hexanes to give 193 mg of methyl 5-(6-bromo-2-(4-fluorophenyl)-1-oxo-1,2-dihydroisoquinolin-3-yl)pentanoate as a yellow oil.

Steps 3 and 4:

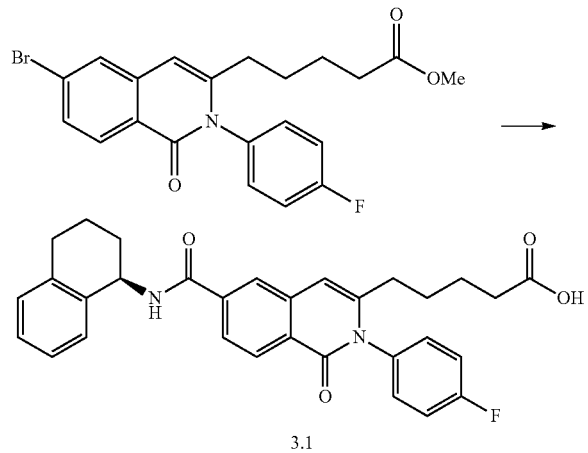

3.1

In a manner similar to that previously described for Example 1, steps 5 and 6, methyl 5-(6-bromo-2-(4-fluorophenyl)-1-oxo-1,2-dihydroisoquinolin-3-yl)pentanoate was aminocarbonylated with (R)-1,2,3,4-tetrahydronaphthalen-1-amine and hydrolyzed with LiOH to provide (R)-5-(2-(4-fluorophenyl)-1-oxo-6-((1,2,3,4-tetrahydronaphthalen-1-yl)carbamoyl)-1,2-dihydroisoquinolin-3-yl)pentanoic acid (3.1). LCMS [M+H]⁺=513. ¹H NMR (DMSO, 500 MHz) δ ppm: 12.00 (br s, 1H), 9.01 (d, 1H, J=8.5 Hz), 8.22-8.16 (m, 2H), 7.92 (d, 1H, J=8.0 Hz), 7.43-7.37 (m, 4H), 7.24-7.13 (m, 3H), 6.66 (s, 1H), 5.30-5.26 (m, 1H), 2.83-2.74 (m, 2H), 2.26-2.23 (m, 2H), 2.12-2.05 (m, 2H), 2.02-2.19 (m, 2H), 1.91-1.76 (m, 2H), 1.42-1.35 (m, 3H), 1.29-1.23 (m, 1H).

The following compound was prepared using a similar procedure as described for Example 3.1 by substituting the appropriates amine for (R)-1,2,3,4-tetrahydronaphthalen-1-amine in step 3.

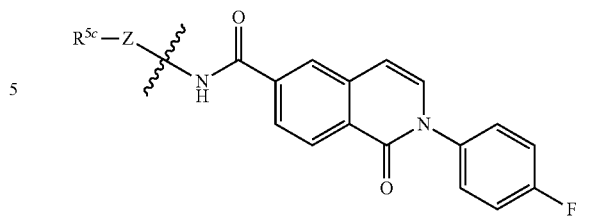

| Ex. No. | Name | R⁵ᶜ—Z— | [M + H]⁺ Obsv'd |
|---|---|---|---|
| 3.2 | (R)-5-(6-((6-fluoro-1,2,3,4-tetrahydronaphthalen-1-yl)carbamoyl)-2-(4-fluorophenyl)-1-oxo-1,2-dihydroisoquinolin-3-yl)pentanoic acid | | 531 |

The following compounds were prepared using a similar procedure as described for Example 3.1 with the following modifications. In step 2, the appropriate substituted aniline was used in place of 4-fluoroaniline. In step 3, (R)-1-(4-fluorophenyl)ethylamine was used in place of (R)-1,2,3,4-tetrahydronaphthalen-1-amine

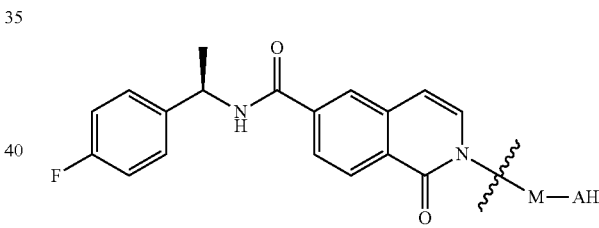

| Ex. No. | Name | —M—AH | [M + H]⁺ Obsv'd |
|---|---|---|---|
| 3.3 | (R)-5-(6-((1-(4-fluorophenyl)ethyl)carbamoyl)-2-(4-methoxyphenyl)-1-oxo-1,2-dihydroisoquinolin-3-yl)pentanoic acid | | 517 |
| 3.4 | (R)-5-(2-(4-cyanophenyl)-6-((1-(4-fluorophenyl)ethyl)carbamoyl)-1-oxo-1,2-dihydroisoquinolin-3-yl)pentanoic acid | | 512 |
| 3.5 | (R)-5-(6-((1-(4-fluorophenyl)ethyl)carbamoyl)-2-(3-methoxyphenyl)-1-oxo-1,2-dihydroisoquinolin-3-yl)pentanoic acid | | 517 |

-continued

| Ex. No. | Name | —M—AH | [M + H]+ Obsv'd |
|---|---|---|---|
| 3.6 | (R)-5-(6-((1-(4-fluorophenyl)ethyl)carbamoyl)-2-(2-methoxyphenyl)-1-oxo-1,2-dihydroisoquinolin-3-yl)pentanoic acid | Rotamer 1* | 517 |
| 3.7 | (R)-5-(6-((1-(4-fluorophenyl)ethyl)carbamoyl)-2-(2-methoxyphenyl)-1-oxo-1,2-dihydroisoquinolin-3-yl)pentanoic acid | Rotamer 2* | 517 |

*Rotamer 1 was the first eluting compound from a silica gel column.

Example 4

Preparation of Compounds of the Invention According to Scheme 1

Example 4.1

(R)-5-(2-(4-fluorophenyl)-6-(4-(4-fluorophenyl)-2-methylpiperazine-1-carbonyl)-1-oxo-1,2-dihydroisoquinolin-3-yl)pentanoic acid Step 1:

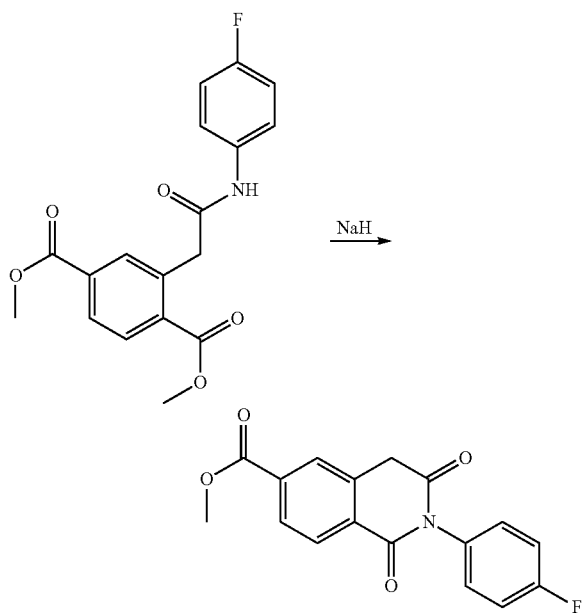

NaH (0.382 g, 9.56 mmol) was added to a stirred, 0° C. mixture of dimethyl 2-(2-((4-fluorophenyl)amino)-2-oxoethyl)terephthalate (1.65 g, 4.78 mmol) in tetrahydrofuran (100 mL) and the mixture was stirred at 0° C. for 90 min. which turned into a red solution. The mixture was diluted with ethyl acetate (30 mL), washed with hydrochloric acid (0.5 M, 1×15 mL), water (10 mL), and brine (20 mL), dried (MgSO₄), filtered and the solvent was evaporated under reduced pressure to give methyl 2-(4-fluorophenyl)-1,3-dioxo-1,2,3,4-tetrahydroisoquinoline-6-carboxylate (1.5 g, 4.79 mmol) as a white solid.

Step 2:

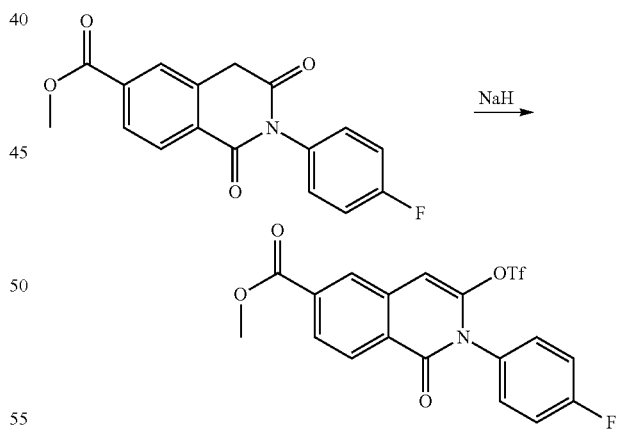

Sodium hydride (0.529 g, 22.03 mmol) was added to a stirred, 0° C. mixture of methyl 2-(4-fluorophenyl)-1,3-dioxo-1,2,3,4-tetrahydroisoquinoline-6-carboxylate (2.3 g, 7.34 mmol) in tetrahydrofuran (130 mL) and the mixture was stirred at 0° C. for 1 h. 2-[N,N-Bis(trifluoromethanesulfonyl)amino]-5-chloropyridine (5.77 g, 14.68 mmol) was added, and the resultant mixture was kept stirring at 0° C. for 1 h, then room temperature for 1 h. The reaction was checked with LCMS and starting material disappeared. The mixture was concentrated, and the residue was purified by column chromatography on silica gel, eluting with EtOAc/isohexane=25% to give methyl 2-(4-fluorophenyl)-1-oxo-3-(((trifluoromethyl)sulfonyl)oxy)-1,2-dihydroisoquinoline-6-carboxylate (2.76 g, 6.20 mmol) as a white solid.

Step 3:

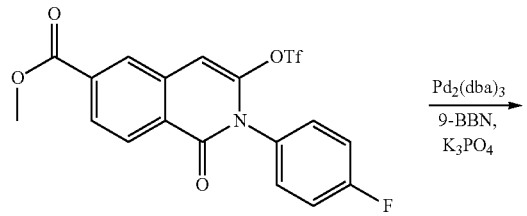

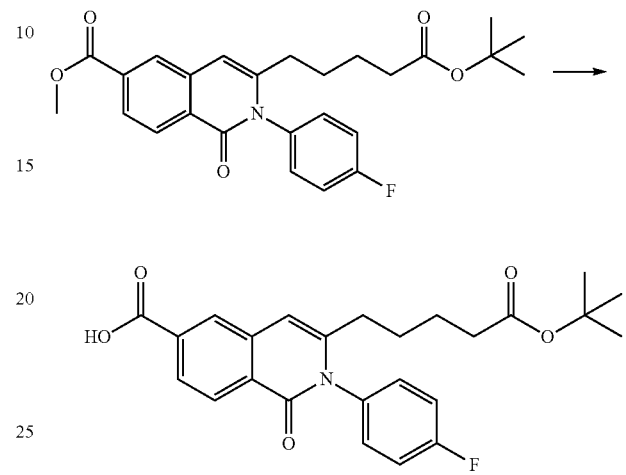

9-Borabicyclo[3.3.1]nonane (20.6 mL, 10.33 mmol) was added to a stirred, 0° C. tert-butyl hex-5-enoate (1.759 g, 10.33 mmol) and the mixture was stirred at room temperature for overnight. The solid mixture of methyl 2-(4-fluorophenyl)-1-oxo-3-(((trifluoromethyl)sulfonyl)oxy)-1,2-dihydroisoquinoline-6-carboxylate (2.3 g, 5.16 mmol), Pd$_2$(dba)$_3$ (0.473 g, 0.516 mmol), Butyl di-1-adamantylphosphine (0.370 g, 1.033 mmol) and potassium phosphate (3.29 g, 15.49 mmol) was added into the liquid mixture, followed by tetrahydrofuran (24 mL), and the resultant mixture was kept stirring at 75° C. for 1 h. The reaction was checked with LCMS and starting material disappeared. The mixture was cooled, diluted with ethyl acetate (100 mL), washed with aqueous ammonium chloride (saturated, 1×40 mL), dried (MgSO$_4$), filtered and the solvent was evaporated under reduced pressure. The residue was purified by column chromatography on silica gel, eluting with EtOAc/isohexane=30% to give a yellow solid (2.62 g). MS showed the material containing about 40% protio product methyl 2-(4-fluorophenyl)-1-oxo-1,2-dihydroisoquinoline-6-carboxylate. SFC separation to give methyl 3-(5-(tert-butoxy)-5-oxopentyl)-2-(4-fluorophenyl)-1-oxo-1,2-dihydroisoquinoline-6-carboxylate (1.24 g, 2.73 mmol) as a light yellow solid and methyl 2-(4-fluorophenyl)-1-oxo-1,2-dihydroisoquinoline-6-carboxylate (0.57 g, 1.917 mmol) as a light yellow solid.

Step 4:

LiOH.H$_2$O (0.229 g, 5.47 mmol) was added to a stirred, room temperature mixture of methyl 3-(5-(tert-butoxy)-5-oxopentyl)-2-(4-fluorophenyl)-1-oxo-1,2-dihydroisoquinoline-6-carboxylate (1.24 g, 2.73 mmol) in MeOH (5 mL), tetrahydrofuran (5.00 mL) and water (5.00 mL) and the mixture was stirred at room temperature for 3 h. The reaction mixture was diluted with diethyl ether (10 mL), water (5 mL) was added, the aqueous layer was separated, acidified with hydrochloric acid (2 M) to pH 2-3, extracted with dichloromethane (2×30 mL), the combined organic was dried (MgSO$_4$), filtered and concentrated to give 3-(5-(tert-butoxy)-5-oxopentyl)-2-(4-fluorophenyl)-1-oxo-1,2-dihydroisoquinoline-6-carboxylic acid (1.153 g, 2.62 mmol) as a yellow solid.

Step 5:

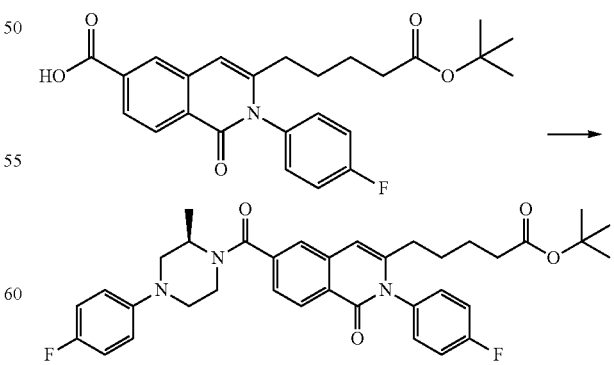

3-(5-(tert-butoxy)-5-oxopentyl)-2-(4-fluorophenyl)-1-oxo-1,2-dihydroisoquinoline-6-carboxylic acid (50 mg, 0.114 mmol)), HOBt.H₂O (34.8, 0.228 mmol), EDCI (43.6 mg, 0.228 mmol), Hunig's base (44.1 mg, 0.341 mmol) and (R)-1-(4-fluorophenyl)-3-methylpiperazine (22.1 mg, 0.114 mmol, prepared from the coupling of (R)-tert-butyl 2-methylpiperazine-1-carboxylate and 1-fluoro-4-iodobenzene using CuI followed with deprotection with TFA) were mixed in dichloromethane (1 mL). The mixture was kept stirring at room temperature for 16 hours before it was diluted with dichloromethane (5 mL), washed with aqueous sodium hydrogen carbonate (saturated, 1×3 mL) and hydrochloric acid (0.5 M, 2 mL), dried (MgSO₄) and filtered. The solvent was evaporated under reduced pressure. The residue was purified by column chromatography on silica gel, eluting with EtOAc/isohexane=1:1 to give (R)-tert-butyl 5-(2-(4-fluorophenyl)-6-(4-(4-fluorophenyl)-2-methylpiperazine-1-carbonyl)-1-oxo-1,2-dihydroisoquinolin-3-yl)pentanoate (58 mg, 0.094 mmol) as a yellow foam.

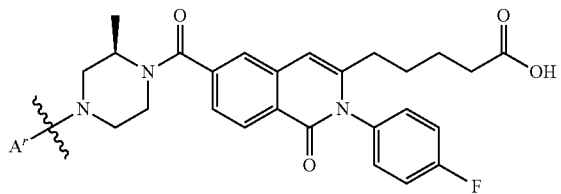

| Ex. No. | Name | A^r | [M + H]⁺ Obsv'd |
|---|---|---|---|
| 4.2 | (R)-5-(2-(4-fluorophenyl)-6-(2-methyl-4-phenylpiperazine-1-carbonyl)-1-oxo-1,2-dihydroisoquinolin-3-yl)pentanoic acid | (phenyl) | 542 |

Step 6:

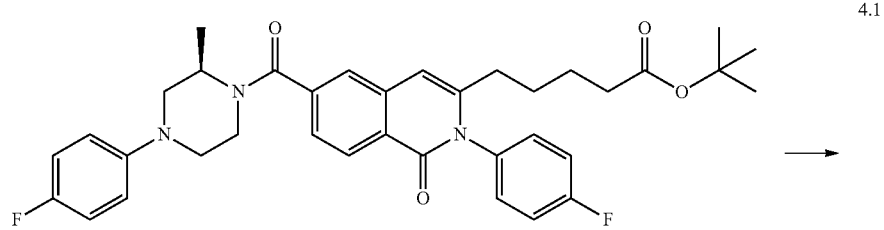

4.1

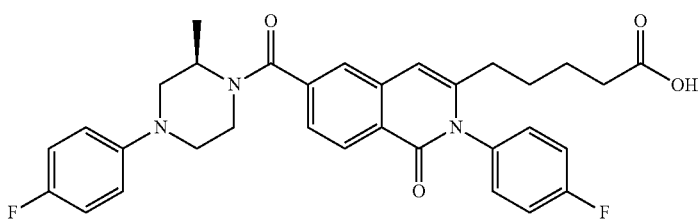

TFA (1 mL, 12.98 mmol) was added to a stirred, room temperature mixture of (R)-tert-butyl 5-(2-(4-fluorophenyl)-6-(4-(4-fluorophenyl)-2-methylpiperazine-1-carbonyl)-1-oxo-1,2-dihydroisoquinolin-3-yl)pentanoate (58 mg, 0.094 mmol) in dichloromethane (4 mL) and the mixture was stirred at room temperature for 2 hours. The mixture was concentrated to dryness, the residue was purified via PTLC (Emerck 1 mm), eluted with CH₂Cl₂/MeOH=10:1 to give (R)-5-(2-(4-fluorophenyl)-6-(4-(4-fluorophenyl)-2-methylpiperazine-1-carbonyl)-1-oxo-1,2-dihydroisoquinolin-3-yl)pentanoic acid (46 mg, 0.082 mmol) as a light yellow solid. LCMS [M+H]⁺=560. ¹H NMR (500 MHz, CDCl₃) δ ppm: 8.43 (d, J=8.28 Hz, 1H), 7.56 (d, J=1.32 Hz, 1H), 7.44 (dd, J=8.28, 1.32 Hz, 1H), 7.26 (m, 2H), 7.25 (m, 2H), 6.96-7.07 (m, 2H), 6.86-6.93 (m, 2H), 6.48 (s, 1H), 3.52 (m, 3H), 2.96 (m, 1H), 2.79 (m, 1H), 2.31 (m, 4H), 1.55-1.68 (m, 6H), 1.50 (d, 3H).

The following compound was prepared using a similar procedure as described for Example 4.1 by substituting (R)-1-phenyl-3-methylpiperazine for (R)-1-(4-fluorophenyl)-3-methylpiperazine in step 3.

The following compounds were prepared using a similar procedure as described for Example 4.1 by substituting corresponding amines for (R)-1-(4-fluorophenyl)-3-methylpiperazine in step 3.

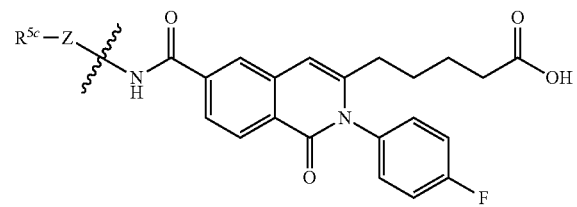

| Ex. No. | Name | $R^{5c}$—Z— | $[M+H]^+$ Obsv'd |
|---|---|---|---|
| 4.3 | 5-(2-(4-fluorophenyl)-1-oxo-6-((2-oxo-1,2,3,4-tetrahydroquinolin-4-yl)carbamoyl)-1,2-dihydroisoquinolin-3-yl)pentanoic acid | 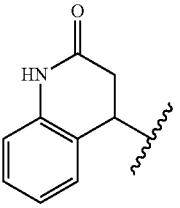 [SMILES: *C1CC(=O)Nc2ccccc21] | 528 |
| 4.4 | (R)-5-(2-(4-fluorophenyl)-6-((1-(4-fluorophenyl)ethyl)carbamoyl)-1-oxo-1,2-dihydroisoquinolin-3-yl)pentanoic acid | 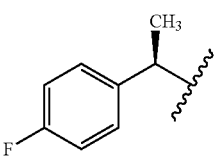 | 505 |

Example 5

Preparation of Compounds of the Invention According to Scheme 2 Wherein $R^1$ is a Substituted Isoxazole Ring

Example 5.1

5-(6-(5-(4-fluorobenzyl)isoxazol-3-yl)-2-(4-fluorophenyl)-1-oxo-1,2-dihydroisoquinolin-3-yl)pentanoic acid Step 1:

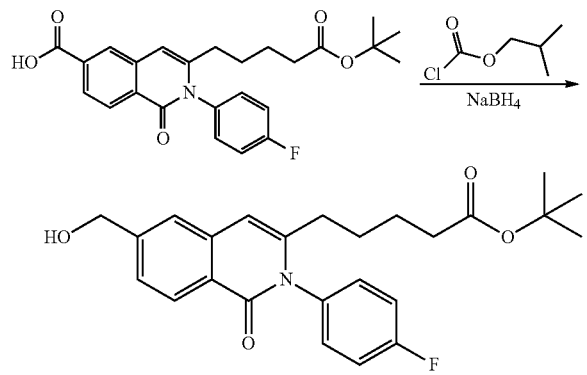

Isobutyl chloroformate (0.285 mL, 2.184 mmol) was added to a stirred, 0° C. mixture of 3-(5-(tert-butoxy)-5-oxopentyl)-2-(4-fluorophenyl)-1-oxo-1,2-dihydroisoquinoline-6-carboxylic acid (800 mg, 1.820 mmol) and Hunig's Base (0.636 mL, 3.64 mmol) in Dichloromethane (20 mL) and the mixture was stirred at 0° C. for 3 h. The mixture was concentrated under reduced pressure with bath temp at 20° C., the residue was taken up in Dichloromethane (20 mL), NaBH$_4$ (138 mg, 3.64 mmol) was added, the mixture was stirred at room temperature for 16 h. MeOH (10 mL) was added, and the resultant mixture was kept stirring at room temperature for 1 h. The mixture was diluted with dichloromethane (60 mL), washed with aqueous sodium hydrogen carbonate (saturated, 1×10 mL), dried (MgSO$_4$), filtered and the solvent was evaporated under reduced pressure. The residue was purified by column chromatography on silica gel, eluting with EtOAc/isohexane=1:1 to give tert-butyl 5-(2-(4-fluorophenyl)-6-(hydroxymethyl)-1-oxo-1,2-dihydroisoquinolin-3-yl)pentanoate (650 mg, 1.528 mmol) as a white solid.

Step 2:

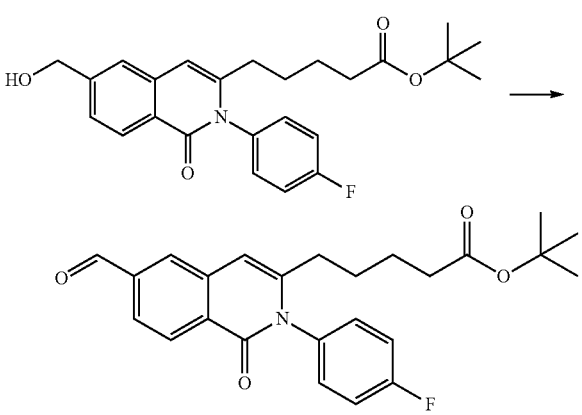

Dess-Martin Periodinane (1296 mg, 3.06 mmol) was added to a stirred, room temperature mixture of tert-butyl 5-(2-(4-fluorophenyl)-6-(hydroxymethyl)-1-oxo-1,2-dihydroisoquinolin-3-yl)pentanoate (650 mg, 1.528 mmol) in dichloromethane (15 mL), and the mixture was stirred at room temperature for 2 h. The mixture was diluted with dichloromethane (20 mL), Na$_2$S$_2$O$_3$ saturated (20 mL) was added, stirred at room temperature for 20 min, the aqueous layer was extracted once more with dichloromethane (15 mL), the combined organic was washed with aqueous sodium hydrogen carbonate saturated (3×15 mL), dried (MgSO$_4$), filtered and concentrated under reduced pressure to give tert-butyl 5-(2-(4-fluorophenyl)-6-formyl-1-oxo-1,2-dihydroisoquinolin-3-yl)pentanoate (638 mg, 1.507 mmol) as a yellow solid.

Step 4:

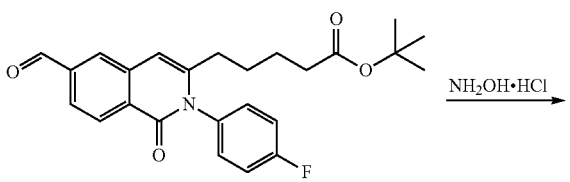

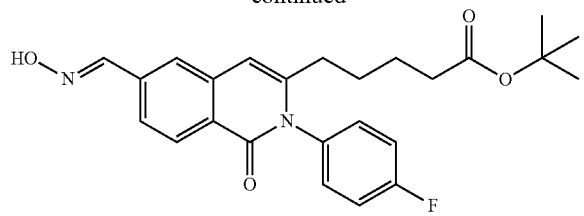

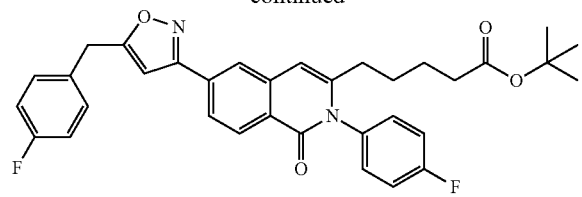

Hydroxylamine hydrochloride (314 mg, 4.52 mmol) was added to a stirred, room temperature mixture of tert-butyl 5-(2-(4-fluorophenyl)-6-formyl-1-oxo-1,2-dihydroisoquinolin-3-yl)pentanoate (638 mg, 1.507 mmol) and sodium acetate (742 mg, 9.04 mmol) in ethanol (10 mL), and the mixture was stirred at room temperature for 1 h. The mixture was diluted with dichloromethane (60 mL), washed with brine (saturated, 1×30 mL), dried (MgSO₄), filtered and the solvent was evaporated under reduced pressure to give tert-butyl 5-(2-(4-fluorophenyl)-6-((hydroxyimino)methyl)-1-oxo-1,2-dihydroisoquinolin-3-yl)pentanoate (658 mg, 1.501 mmol) as a white solid.

Step 5:

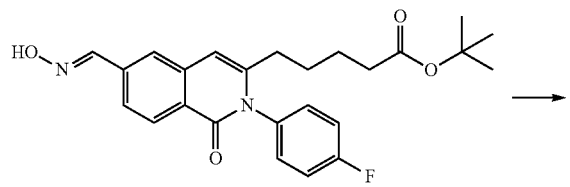

Sodium hypochlorite (1.408 mL, 0.912 mmol) was added to a stirred, room temperature mixture of tert-butyl 5-(2-(4-fluorophenyl)-6-((hydroxyimino)methyl)-1-oxo-1,2-dihydroisoquinolin-3-yl)pentanoate (100 mg, 0.228 mmol) and 1-fluoro-4-(prop-2-ynyl)benzene (61.2 mg, 0.456 mmol) in dichloromethane (2 mL), and the mixture was stirred at room temperature for overnight. The reaction was checked with LCMS and starting material was all consumed. The mixture was diluted with dichloromethane (10 mL), washed with aqueous sodium hydrogen carbonate (saturated, 1×8 mL), dried (MgSO₄), filtered and the solvent was evaporated under reduced pressure. The residue was purified by column chromatography on silica gel, eluting with EtOAc/isohexane=50% to give tert-butyl 5-(6-(5-(4-fluorobenzyl)isoxazol-3-yl)-2-(4-fluorophenyl)-1-oxo-1,2-dihydroisoquinolin-3-yl)pentanoate (102 mg, 0.179 mmol) as a yellow solid.

Step 6:

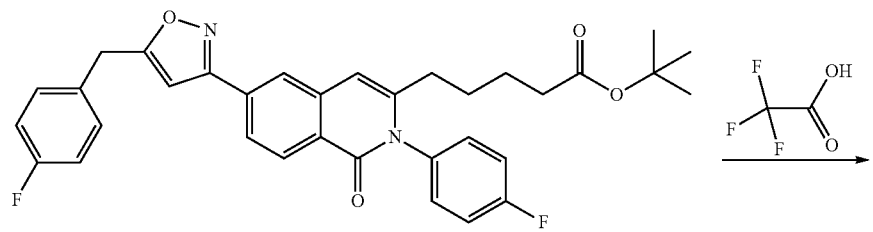

5.1

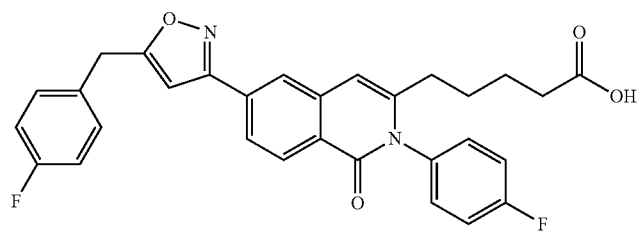

TFA (2 mL, 26.0 mmol) was added to a stirred, room temperature mixture of tert-butyl 5-(6-(5-(4-fluorobenzyl)isoxazol-3-yl)-2-(4-fluorophenyl)-1-oxo-1,2-dihydroisoquinolin-3-yl)pentanoate (100 mg, 0.175 mmol) in dichloromethane (2 mL) and the mixture was stirred at room temperature for 2 h. The reaction mixture was concentrated to dryness and the residue was purified by column chromatography on silica gel, eluting with $CH_2Cl_2$/MeOH=10:1 to give 5-(6-(5-(4-fluorobenzyl)isoxazol-3-yl)-2-(4-fluorophenyl)-1-oxo-1,2-dihydroisoquinolin-3-yl)pentanoic acid (75 mg, 0.146 mmol) as a yellow solid. LCMS [M+H]$^+$=515. 1H NMR (500 MHz, CDCl$_3$) δ ppm: 8.42 (d, J=8.51 Hz, 1H), 7.93 (d, J=1.26 Hz, 1H), 7.81 (d, J=1.58 Hz, 1H), 7.17-7.37 (m, 6H), 7.09 (t, J=8.51 Hz, 2H), 6.49 (s, 1H), 6.33 (s, 1H), 4.17 (s, 2H), 2.22-2.39 (m, 4H), 1.38-1.65 (m, 4H).

Example 6

Preparation of Compounds of the Invention According to Scheme 2 where Le is a Substituted Isoxazoline Ring

Examples 6.1 and 6.2

5-(4-chloro-6-(5-(6-fluorobenzo[d]oxazol-2-yl)-5-methyl-4,5-dihydroisoxazol-3-yl)-2-(4-fluorophenyl)-1-oxo-1,2-dihydroisoquinolin-3-yl)pentanoic acid (6.1) and 5-(6-(5-(6-fluorobenzo[d]oxazol-2-yl)-5-methyl-4,5-dihydroisoxazol-3-yl)-2-(4-fluorophenyl)-1-oxo-1,2-dihydroisoquinolin-3-yl)pentanoic acid (6.2)

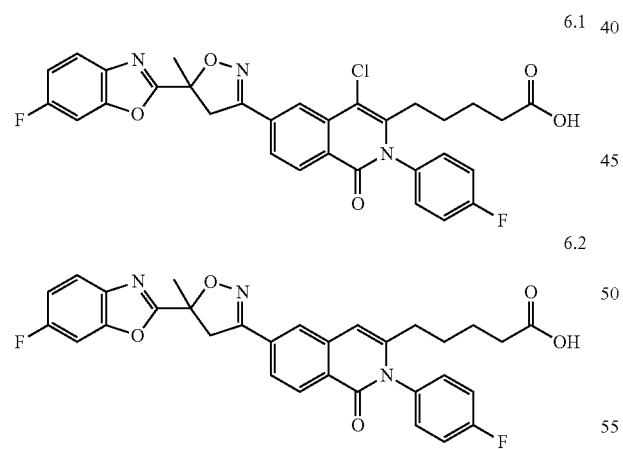

Sodium hypochlorite (1.408 mL, 0.912 mmol) was added to a stirred, room temperature mixture of (E)-tert-butyl 5-(2-(4-fluorophenyl)-6-((hydroxyimino)methyl)-1-oxo-1,2-dihydroisoquinolin-3-yl)pentanoate (100 mg, 0.228 mmol) and 6-fluoro-2-(prop-1-en-2-yl)benzo[d]oxazole (40.4 mg, 0.228 mmol) in dichloromethane (2 mL) and the mixture was stirred at room temperature for overnight. The reaction was checked with LCMS and starting material was all consumed. The mixture was diluted with dichloromethane (10 mL), washed with aqueous sodium hydrogen carbonate (saturated, 1×6 mL), dried (MgSO$_4$), filtered and the solvent was evaporated under reduced pressure. The residue was purified by column chromatography on silica gel, eluting with EtOAc/isohexane=50% to give tert-butyl 5-(4-chloro-6-(5-(6-fluorobenzo[d]oxazol-2-yl)-5-methyl-4,5-dihydroisoxazol-3-yl)-2-(4-fluorophenyl)-1-oxo-1,2-dihydroisoquinolin-3-yl)pentanoate (48 mg, 0.074 mmol) as a yellow solid, 648.0 (M+H$^+$); and tert-butyl 5-(6-(5-(6-fluorobenzo[d]oxazol-2-yl)-5-methyl-4,5-dihydroisoxazol-3-yl)-2-(4-fluorophenyl)-1-oxo-1,2-dihydroisoquinolin-3-yl)pentanoate (26 mg, 0.042 mmol) as a yellow solid which were deprotected with TFA as in Example 5.1 to give Examples 6.1 and 6.2 respectively.

Example 6.1

LCMS [M+H]$^+$=648. $^1$H NMR (500 MHz, CDCl$_3$) δ ppm: 8.45 (d, J=8.23 Hz, 1H), 8.20 (d, J=1.40 Hz, 1H), 7.98 (dd, J=8.23, 1.56 Hz, 1H), 7.65-7.75 (m, 1H), 7.24-7.38 (m, 5H), 7.12-7.19 (m, 1H), 4.47 (d, J=16.7 Hz, 1H), 3.64 (d, J=16.7 Hz, 1H), 2.55-2.70 (m, 2H), 2.19-2.32 (m, 2H), 2.10 (s, 3H), 1.61 (m, 4H).

Example 6.2

LCMS [M+H]$^+$=614. $^1$H NMR (500 MHz, CDCl$_3$) δ ppm: 8.41 (d, J=8.20 Hz, 1H), 7.75-7.86 (m, 2H), 7.69 (dd, J=8.83, 4.73 Hz, 1H), 7.06-7.38 (m, 6H), 6.48 (s, 1H), 4.41 (d, J=17.02 Hz, 1H), 3.57 (d, J=16.71 Hz, 1H), 2.28-2.35 (m, 4H), 2.05-2.11 (m, 3H), 1.54-1.62 (m, 4H).

Example 7

Preparation of Compounds of the Invention According to Scheme 3 where R$^1$ is a Substituted Oxadiazole Ring

Example 7.1

5-(6-(5-(2,3-dihydro-1H-inden-2-yl)-1,2,4-oxadiazol-3-yl)-2-(4-fluorophenyl)-1-oxo-1,2-dihydroisoquinolin-3-yl)pentanoic acid Step 1:

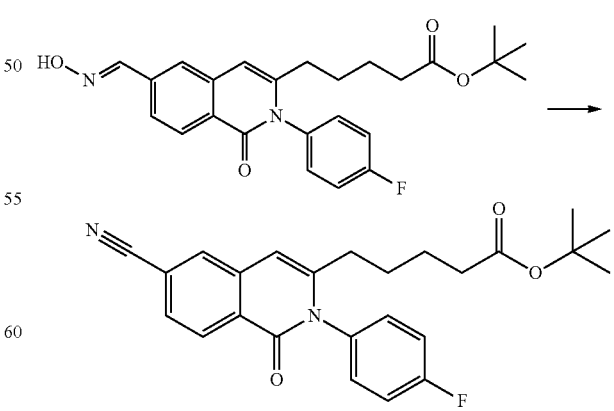

1,2-di-(1H-imidazol-1-yl)ethane-1,2-dione (130 mg, 0.684 mmol) was added to a stirred, room temperature mixture of tert-butyl 5-(2-(4-fluorophenyl)-6-((hydroxyimino)

methyl)-1-oxo-1,2-dihydroisoquinolin-3-yl)pentanoate (200 mg, 0.456 mmol) in toluene (6.00 mL) and 1,2-dichloroethane (2 mL) and the mixture was stirred at 80° C. for 2 h. The mixture was cooled, diluted with ethyl acetate (20 mL), washed with aqueous sodium hydrogen carbonate (1 M, 1×15 mL), dried (MgSO₄), filtered and the solvent was evaporated under reduced pressure to give tert-butyl 5-(6-cyano-2-(4-fluorophenyl)-1-oxo-1,2-dihydroisoquinolin-3-yl)pentanoate (185 mg, 0.440 mmol) as a yellow gum.

Step 2:

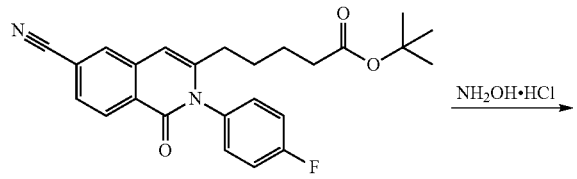

NH₂OH·HCl →

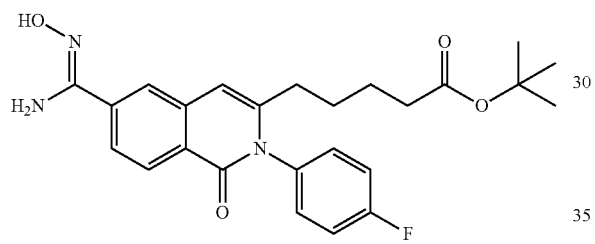

Hydroxylamine hydrochloride (183 mg, 2.64 mmol) was added to a stirred, room temperature mixture of tert-butyl 5-(6-cyano-2-(4-fluorophenyl)-1-oxo-1,2-dihydroisoquinolin-3-yl)pentanoate (185 mg, 0.440 mmol) and K₂CO₃ (365 mg, 2.64 mmol) in MeOH (20 mL) and the mixture was stirred at room temperature for overnight. The mixture was diluted with dichloromethane (60 mL), washed with aqueous ammonium chloride (saturated, 1×20 mL), dried (MgSO₄), filtered and the solvent was evaporated under reduced pressure to give tert-butyl 5-(2-(4-fluorophenyl)-6-(N'-hydroxycarbamimidoyl)-1-oxo-1,2-dihydroisoquinolin-3-yl)pentanoate (200 mg, 0.441 mmol) as an off white solid.

Step 3:

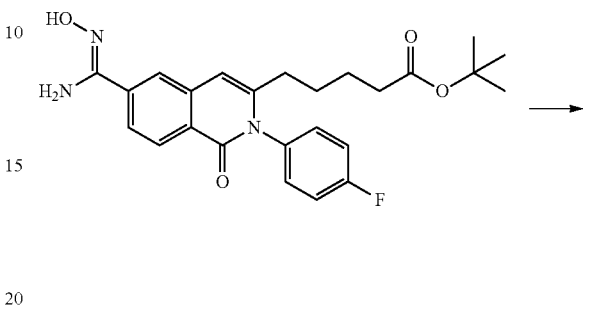

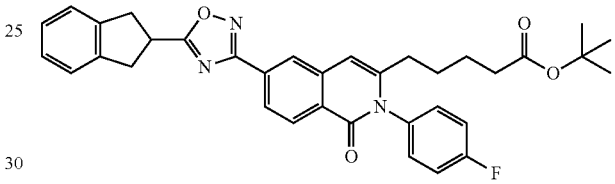

CDI (21.45 mg, 0.132 mmol) was added to a stirred, room temperature mixture of 2-indanecarboxylic acid (17.88 mg, 0.110 mmol) in DMF (1 mL), and the mixture was stirred at room temperature for 2 h. tert-butyl 5-(2-(4-fluorophenyl)-6-(N'-hydroxycarbamimidoyl)-1-oxo-1,2-dihydroisoquinolin-3-yl)pentanoate (50 mg, 0.110 mmol) was added, and the resultant mixture was kept stirring at 100° C. for overnight. The reaction was checked with LCMS and starting material disappeared. The mixture was cooled to room temperature, precipitate formed, filtered and washed with water (20 mL), dried in vacuum oven to give tert-butyl 5-(6-(5-(2,3-dihydro-1H-inden-2-yl)-1,2,4-oxadiazol-3-yl)-2-(4-fluorophenyl)-1-oxo-1,2-dihydroisoquinolin-3-yl)pentanoate (51 mg, 0.088 mmol) as a light tan solid.

Step 4:

7.1

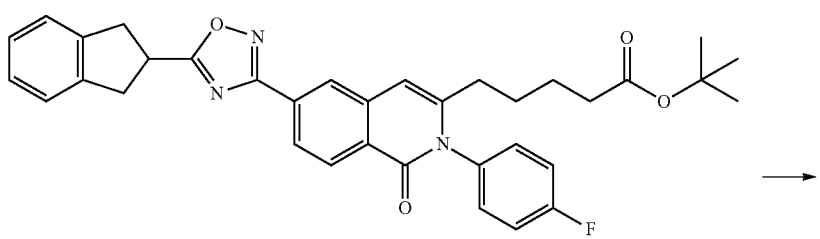

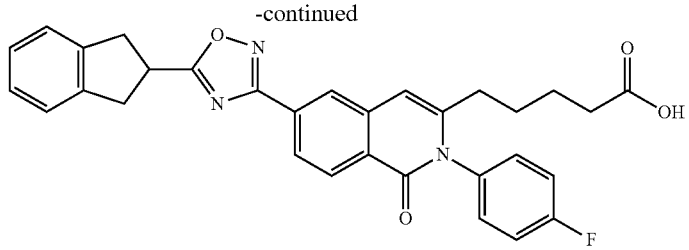

Tert-butyl 5-(6-(5-(2,3-dihydro-1H-inden-2-yl)-1,2,4-oxadiazol-3-yl)-2-(4-fluorophenyl)-1-oxo-1,2-dihydroisoquinolin-3-yl)pentanoate was deprotected with TFA as in Example 5.1 to give Example 7.1. LCMS [M+H]$^+$=580. $^1$H NMR (500 MHz, CDCl$_3$) δ ppm: 8.47 (d, J=8.20 Hz, 1H), 8.27 (d, J=1.20 Hz, 1H), 7.69 (dd, J=8.20, 1.58 Hz, 1H), 7.20-7.38 (m, 8H), 6.54 (s, 1H), 4.01-4.11 (m, 1H), 3.56 (d, J=8.51 Hz, 4H), 2.32 (m, 4H), 1.60 (m, 4H).

The following compounds were prepared using a similar procedure as described for Example 7.1 by substituting appropriate carboxylic acids for 2-indanecarboxylic acid in step 3.

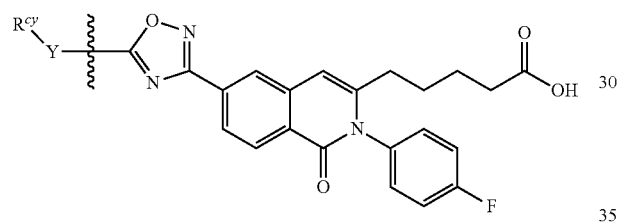

| Ex. No. | Name | R$^{cy}$—Y— | [M + H]$^+$ Obsv'd |
|---|---|---|---|
| 7.2 | 5-(6-(5-(4-fluorobenzyl)-1,2,4-oxadiazol-3-yl)-2-(4-fluorophenyl)-1-oxo-1,2-dihydroisoquinolin-3-yl)pentanoic acid | 4-F-C$_6$H$_4$-CH$_2$- | 517 |
| 7.3 | 5-(2-(4-fluorophenyl)-6-(5-(1-(4-fluorophenyl)ethyl)-1,2,4-oxadiazol-3-yl)-1-oxo-1,2-dihydroisoquinolin-3-yl)pentanoic acid | 4-F-C$_6$H$_4$-CH(CH$_3$)- | 530 |
| 7.4 | 5-(2-(4-fluorophenyl)-1-oxo-6-(5-(4-(trifluoromethyl)phenyl)-1,2,4-oxadiazol-3-yl)-1,2-dihydroisoquinolin-3-yl)pentanoic acid | 4-CF$_3$-C$_6$H$_4$- | 552 |

Example 8

Preparation of Compounds According to Scheme 4

Example 8.1

(R)-3-(5-(cyclopropanesulfonamido)-5-oxopentyl)-N-(6-fluoro-1,2,3,4-tetrahydronaphthalen-1-yl)-2-(4-fluorophenyl)-1-oxo-1,2-dihydroisoquinoline-6-carboxamide

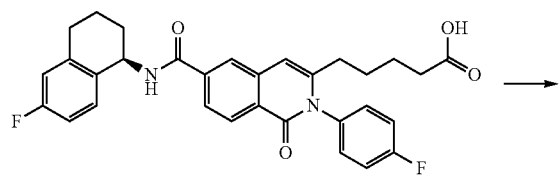

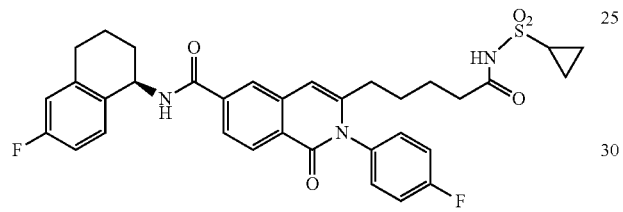

A mixture of (R)-5-(6-((6-fluoro-1,2,3,4-tetrahydronaphthalen-1-yl)carbamoyl)-2-(4-fluorophenyl)-1-oxo-1,2-dihydroisoquinolin-3-yl)pentanoic acid (10 mg, 0.019 mmol), cyclopropanesulfonamide (3.43 mg, 0.028 mmol, 1.50 equiv.), DMAP (4.61 mg, 0.038 mmol, 2.0 equiv.) and EDC (7.23 mg, 0.038 mmol, 2.0 equiv.) in DCM (1 mL) was stirred at room temperature overnight. The residue was purified by column chromatography on silica gel eluting with 0-3% $CH_2Cl_2$/MeOH to give 7.8 mg of (R)-3-(5-(cyclopropanesulfonamido)-5-oxopentyl)-N-(6-fluoro-1,2,3,4-tetrahydronaphthalen-1-yl)-2-(4-fluorophenyl)-1-oxo-1,2-dihydroisoquinoline-6-carboxamide as a white solid. LCMS [M+H]$^+$=634. $^1$H NMR (DMSO, 500 MHz) δ ppm: 8.18 (dd, J=8.0, 3.5 Hz, 2H), 7.91 (d, J=8.0 Hz, 1H), 7.43-7.36 (m, 4H), 7.26 (t, J=7.0 Hz, 1H), 7.00 (t, J=8.5 Hz, 2H), 6.66 (s, 1H), 5.26-5.22 (m, 1H), 2.85-2.74 (m, 3H), 2.30-2.15 (m, 4H), 2.09 (t, J=7.0 Hz, 2H), 2.00-1.96 (m, 2H), 1.91-1.76 (m, 2H), 1.45-1.39 (m, 4H), 1.10-1.00 (m, 4H).

Example 8.2

(R)-3-(5-(cyclopropanesulfonamido)-5-oxopentyl)-2-(4-fluorophenyl)-N-(1-(4-fluorophenyl)ethyl)-1-oxo-1,2-dihydroisoquinoline-6-carboxamide

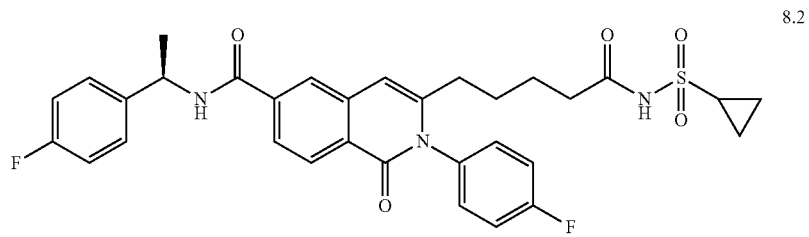 [SMILES: C[C@@H](NC(=O)c1ccc2c(=O)n(-c3ccc(F)cc3)c(CCCCC(=O)NS(=O)(=O)C3CC3)cc2c1)c1ccc(F)cc1]

CDI (13.50 mg, 0.083 mmol) was added to a stirred, room temperature mixture of (R)-5-(2-(4-fluorophenyl)-6-((1-(4-fluorophenyl)ethyl)carbamoyl)-1-oxo-1,2-dihydroisoquinolin-3-yl)pentanoic acid (28 mg, 0.055 mmol) in tetrahydrofuran (2 mL) and the mixture was stirred at 70° C. for 2 h. DBU (0.017 mL, 0.111 mmol) and cyclopropylsulfonamide (10.09 mg, 0.083 mmol) were added, the resultant mixture was kept stirring at room temperature overnight. The mixture was concentrated, and the residue was purified via PTLC (Emerck 1 mm), eluted with $CH_2Cl_2$/MeOH=10:1 to give (R)-3-(5-(cyclopropanesulfonamido)-5-oxopentyl)-2-(4-fluorophenyl)-N-(1-(4-fluorophenyl)ethyl)-1-oxo-1,2-dihydroisoquinoline-6-carboxamide (16 mg) as a white solid. LCMS [M+H]$^+$=608. $^1$H NMR (500 MHz, DMSO) δ ppm: 9.06 (d, J=7.88 Hz, 1H), 8.20 (d, J=8.20 Hz, 1H), 8.15 (s, 1H), 7.36-7.50 (m, 6H), 7.18 (t, J=8.99 Hz, 2H), 6.69 (s, 1H), 5.22 (t, J=7.25 Hz, 1H), 3.16-3.19 (m, 1H), 2.87-2.94 (m, 1H), 2.26 (br. s, 2H), 2.16 (br. s, 2H), 1.51 (d, J=7.25 Hz, 3H), 1.43 (br. s, 3H), 0.98-1.05 (m, 4H).

The following compounds were prepared using similar procedures as described for Examples 8.1 and 8.2 from the appropriate carboxylic acid precursor in the coupling reaction.

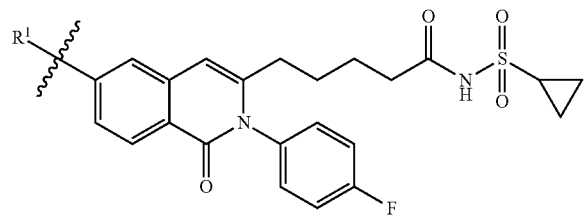

ug of membrane protein prepared from a human embryonic kidney (HEK)-hCRTH$_2$ cell line adhered to 140 ug of wheat-germ agglutinin SPA beads (PerkinElmer). Total and non-specific binding were determined in the absence and the presence of a CRTH$_2$ antagonist, respectively. The reaction was routinely conducted for 60 minutes at room temperature followed by centrifugation for 5 minutes at 1000 RPM. The radioactivity was measured with a TopCountNXT (PerkinElmer). Filtration binding assays were done in a similar way with minor differences. The assay volume was 0.20 mL and competing ligands in dimethylsulfoxide were added in 2 uL. [$^3$H]-PGD$_2$ was used at 0.6 nM, and reactions were initiated by the addition of 10 ug of membrane protein. Reactions were terminated by filtration through GF/C filter plates (PerkinElmer) presoaked in 10 mM HEPES. After washing with buffer, plates were dried in a 50° C. oven for 1 h, scintillation

| Ex. No. | Name | R$^1$ | [M + H]$^+$ Obsv'd |
|---|---|---|---|
| 8.3 | (R)-N-(cyclopropylsulfonyl)-5-(2-(4-fluorophenyl)-6-(4-(4-fluorophenyl)-2-methylpiperazine-1-carbonyl)-1-oxo-1,2-dihydroisoquinolin-3-yl)pentanamide | | 663 |
| 8.4 | (R)-N-(cyclopropylsulfonyl)-5-(2-(4-fluorophenyl)-6-(2-methyl-4-phenylpiperazine-1-carbonyl)-1-oxo-1,2-dihydroisoquinolin-3-yl)pentanamide | | 645 |
| 8.5 | N-(cyclopropylsulfonyl)-5-(6-(5-(4-fluorobenzyl)isoxazol-3-yl)-2-(4-fluorophenyl)-1-oxo-1,2-dihydroisoquinolin-3-yl)pentanamide | | 618 |
| 8.6 | N-(cyclopropylsulfonyl)-5-(6-(5-(4-fluorobenzyl)-1,2,4-oxadiazol-3-yl)-2-(4-fluorophenyl)-1-oxo-1,2-dihydroisoquinolin-3-yl)pentanamide | | 619 |

BIOLOGICAL ASSAYS

Radioligand Binding Assay

Radioligand binding was performed using filtration or scintillation proximity assay (SPA) technology. SPA assays were done at room temperature in 10 mM HEPES pH 7.4, 1 mM EDTA containing 2 mM MnCl$_2$ and 16 nM [$^3$H]-PGD$_2$ (PerkinElmer, Waltham, Mass.) (164 Ci mmol-1), in a final volume of 0.05 mL. Competing ligands were diluted in dimethylsulfoxide and added using very low volumes (500 nL). The reaction was initiated by the addition of a mixture of 3.52 cocktail was added and radioactivity was measured. Results determined using the SPA-based assay were similar to those from the filtration binding assay. Table A (below) sets forth the results of the binding assay for representative compounds of the invention.

TABLE A

| Ex. No. | Ki (nM) |
|---|---|
| 1.1 | 37.67 |
| 1.2 | 49.04 |

TABLE A-continued

| Ex. No. | Ki (nM) |
|---|---|
| 2.1 | 4921 |
| 3.1 | 5.788 |
| 3.2 | 6.504 |
| 3.3 | 8.202 |
| 3.4 | 8.838 |
| 3.5 | 13.05 |
| 3.6 | 363.1 |
| 3.7 | 18.74 |
| 4.1 | 22.51 |
| 4.2 | 13.55 |
| 4.3 | 20.7 |
| 4.4 | 5.159 |
| 5.1 | 10.17 |
| 6.1 | 79.08 |
| 6.2 | 25.45 |
| 7.1 | 21.54 |
| 7.2 | 7.793 |
| 7.3 | 12.72 |
| 7.4 | 14.8 |
| 8.1 | 10.91 |
| 8.2 | 14.8 |
| 8.3 | 17.03 |
| 8.4 | 37.16 |
| 8.5 | 17.16 |
| 8.6 | 17.33 | i[cAMP] Measurements.

The ability of the compounds to antagonize the formation of cAMP can be assayed using the ELISA-based assay described in this example. HEK-hCRTH$_2$ cells are grown to 80-90% confluency. On the day of the assay, the cells are washed with phosphate buffered saline (PBS), incubated for 2 min in cell dissociation buffer, harvested by centrifugation at 300 g for 7 min at room temperature and resuspended at 1.25e10$^6$ cells mL$^{-1}$ in Hanks' balanced salt solution containing 20 mM HEPES pH 7.4 and 0.75 mM IBMX (HBSS/HEPES/IBMX). The assay is performed in 384-plate format with 0.01 mL HBSS/HEPES/IBMX per well containing 12 500 cells and 70 to 75 nl of the test compound and DK-PGD$_2$ at various concentrations. Following a 0 to 10 to min preincubation of the cells with the test compound at 37° C., 0.005 mL of 30 μM Forskolin dilute in HBSS 20 mM HEPES, is added at a final concentration of 10 uM to initiate the reaction. After 10 to 60 min incubation at room temperature or 37° C., the cAMP content was quantified using the cAMP XS+ HitHunter chemiluminescence assay (GE Healthcare 90-0075). Percent inhibition is calculated using the Forskolin and EC85 DK-PGD$_2$ controls.

β-Arrestin assay:

CHO-K1 cells obtained from DiscoverX are stably transfected with human CRTH$_2$ (propagation medium: F-12, 10% FBS, 300 ug/mL hygB and 800 ug/mL G418). Cells are grown in T175 cm$^2$ flask. While in log phase, cells are collected via 0.05% trypsin treatment. Triturated cells are filtered and 40 uL (10K cells) are plated per well in a 384-well white clear bottom plate and incubated 0/N. Cell plate is emptied via inversion and blotted dry. Each well is filled with 35 uL of HBSS (with Ca$^{++}$ and Mg$^{++}$) and incubated for 5 min. Compounds are added in volumes of 1 μL and the plate is gently shaken for 2 min., followed by incubation at 37° C. for 20 min. All compounds and controls are diluted in HBSS assay buffer (with Ca$^{++}$ and Mg$^{++}$) with a final concentration range of 10$^{-5}$ M to 3×10$^{-11}$ M, 11 point Dose response curves at appropriate half-log increments. Final DMSO % is ≤0.3%. Agonist Assay: 1 μl/well of compound is added into cell plate and left to incubate at 37° C. for 90 min. Antagonist Assay: 1 μl/well of compounds are added into a cell plate. Incubate 30 minutes at 37° C. Stimulate cells with 1 ul/well of PGD$_2$ [100 nM] final. Incubate plate for 60 minutes at 37° C. Resulting luminescent signal is detected via Discoverx PathHunter Detection Kit per manufacturer's instructions. A total of 12 μl/well is added to each well. The plate is covered and incubated for 60 min. with gentle shaking. Chemiluminescent detection is done by a SpectraMax plate reader.

Eosinophil Shape Change Assay in Human Whole Blood:

Blood is collected in vacutainers containing EDTA. The antagonist is added to blood and incubated for 10 min at room temperature. DK-PGD$_2$ (13,14-dihydro-15-keto prostaglandin D$_2$) are then added to blood for 4 min at 37° C. in a running water bath. Blood cells are then fixed in presence of cold 0.25%(v/v) paraformaldehyde prepared in 75%(v/v) DPBS without Ca$^{++}$ and Mg$^{++}$ for 1 min on ice. 175 μL of fixed blood is transferred into 870 μL of cold 155 mM NH$_4$Cl lysis solution and incubated at 4° C. for at least 40 min. The solution is then centrifuged at 430 g for 5 min and the supernatant is discarded. Centrifuged cells are resuspended in residual supernatant and sodium azide is added (1% final concentration). Samples are analyzed with a FACs Calibur flow cytometer (Becton Dickinson). Flow cytometry raw data is analyzed with Diva software by isolating the eosinophils from the neutrophils based on their high autofluorescence and determining the percent of total eosinophils with increased forward light scatter. Maximum (100%) and minimum (0%) shape change is determined in the presence of 10 μM DK-PGD$_2$ and DPBS, respectively. A dose response curve with DK-PGD$_2$ is performed with every assay to determine the EC$_{50}$ for each blood donor. Compounds are tested in 11-dose titration curves in the presence of 50 nM DK-PGD$_2$ to determine an antagonist IC$_{50}$.

While the present invention has been described in conjunction with the specific embodiments set forth above, many alternatives, modifications and other variations thereof will be apparent to those of ordinary skill in the art. All such alternatives, modifications and variations are intended to fall within the spirit and scope of the present invention.

What is claimed is:

1. A compound of the Formula (I)

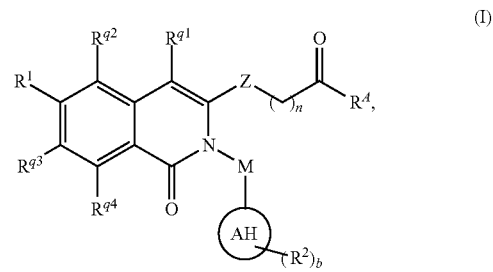

wherein:

Z is a bond or —N(H)—;

R$^A$ is —OH, —N(H)—S(O)$_2$—R$^{A1}$, or —N(H)—S(O)$_2$—N(H)R$^{A1}$

R$^{A1}$ is C$_1$-C$_6$ alkyl, C$_3$-C$_6$ cycloalkyl, or phenyl, wherein R$^{A1}$ is unsubstituted or substituted by 1 to 3 fluoro or C$_1$-C$_3$ alkyl;

the subscript n is 1, 2, 3, or 4;

M is a bond or C$_1$-C$_3$ alkylene;

ring AH is
A phenyl; or
B a 5- to 6-membered heteroaryl containing 1 to 3 heteroatoms selected from the group consisting of N, O, and S;

each $R^2$ is independently selected from the group consisting of halo, $C_1$-$C_3$ alkyl, $C_1$-$C_3$ fluoroalkyl, $C_3$-$C_6$ cycloalkyl, $C_1$-$C_3$ alkoxy, and —CN;

the subscript b is 0, 1, 2, 3, 4, or 5;

$R^{q1}$, $R^{q2}$, $R^{q3}$, and $R^{q4}$ are independently selected from the group consisting of H, halo, and $C_1$-$C_3$ alkyl;

$R^1$ is
A group of the formula —C(O)N($R^3$)($R^4$), wherein
1) $R^3$ and $R^4$ are independently
(a) H, or
(b) —Z—$R^{5C}$, wherein
Z is a bond or $C_1$-$C_3$ alkylene;
$R^{5C}$ is
(i) $C_5$-$C_{10}$ mono or bicyclic carbocyclyl,
(ii) 5- to 10-membered mono- or bicyclic heterocyclyl containing 1 to 3 heteroatoms selected from N and O;
(iii) 5- to 10-membered mono or bicyclic heteroaryl containing 1 to 3 heteroatoms selected from N and O;
wherein said carbocyclyl, heterocyclyl, and heteroaryl of $R^{5C}$ is unsubstituted or substituted by 1 to 4 $R^{5A}$ moieties selected from the group consisting of halo, $C_1$-$C_3$ alkyl, $C_1$-$C_3$ fluoroalkyl, $C_1$-$C_3$ alkoxy, and —CN; or
2) $R^3$ and $R^4$ together with the N atom to which they are attached form $R^{5H}$, wherein $R^{5H}$ is selected from the group consisting of:

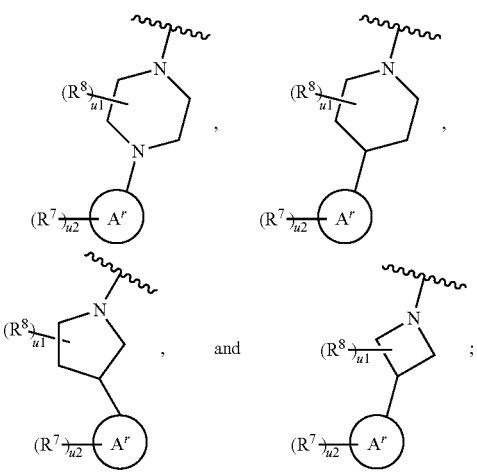

ring $A^r$ is aryl, pyridyl, or pyrimidyl;
each $R^7$ is independently selected from the group consisting of halo, $C_1$-$C_3$ alkyl, $C_1$-$C_3$ fluoroalkyl, $C_1$-$C_3$ alkoxy, and —CN;
each $R^8$ is independently selected from the group consisting of H and $C_1$-$C_3$ alkyl;
the subscript u1 is 0, 1 or 2;
the subscript u2 is 0, 1, 2, or 3; or B) a moiety selected from the group consisting of:

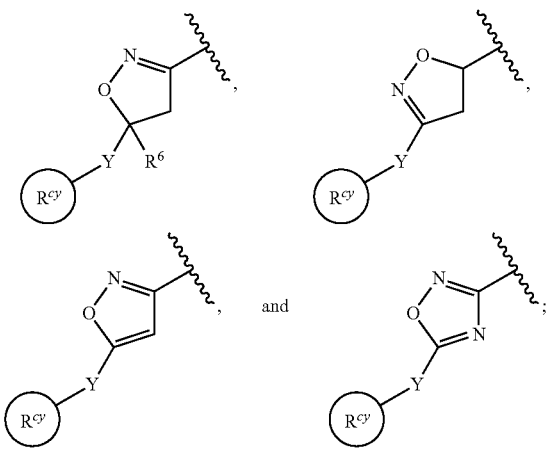

Y is a bond or $C_1$-$C_3$ alkylene;
$R^6$ is H, $C_1$-$C_3$ alkyl, or $C_3$-$C_6$ cycloalkyl;
$R^{cy}$ is:
1) $C_6$-$C_{10}$ mono or bicyclic carbocyclyl;
2) 5- to 9-membered mono- or bicyclic heterocyclyl containing 1 to 3 heteroatoms selected from the group consisting of N and O;
3) 5- to 9-membered mono- or bicyclic heteroaryl containing 1 to 3 heteroatoms selected N and O;
wherein $R^{cy}$ is unsubstituted or substituted by 1 to 3 $R^9$ moieties which are independently selected from the group consisting of halo, $C_1$-$C_3$ alkyl, $C_1$-$C_3$ fluoroalkyl, $C_1$-$C_3$ alkoxy, and —CN, or wherein two $R^9$ moieties are geminally substituted on a common ring carbon of $R^{cy}$, the two geminally substituted $R^9$ moieties, together with said common carbon atom, form —C(O)—;

or a pharmaceutically acceptable salt thereof.

2. The compound of claim 1 or a pharmaceutically acceptable salt thereof, wherein $R^1$ is the group of the formula —C(O)N($R^3$)($R^4$).

3. The compound of claim 1 or a pharmaceutically acceptable salt thereof, wherein $R^3$ is —Z—$R^{5C}$ and $R^4$ is H.

4. The compound of claim 3 or a pharmaceutically acceptable salt thereof, wherein
Z is a bond or

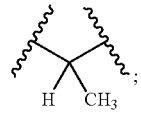

and
$R^{5C}$ is $C_6$-$C_{10}$ carbocyclyl, wherein said $C_6$-$C_{10}$ carbocyclyl is unsubstituted or substituted by 1 to 4 $R^{5A}$ moieties.

5. The compound of claim 4 or a pharmaceutically acceptable salt thereof, wherein said $C_6$-$C_{10}$ carbocyclyl is selected from the group consisting of phenyl, indanyl or tetrahydronaphthalenyl.

6. The compound of claim 1 or a pharmaceutically acceptable salt thereof, wherein $R^3$ and $R^4$ together with the N atom to which they are attached form $R^{5H}$.

7. The compound of claim 6 or a pharmaceutically acceptable salt thereof, wherein $R^{5H}$ is

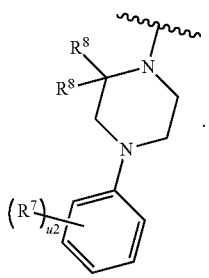

8. The compound of claim 1 or a pharmaceutically acceptable salt thereof, wherein $R^1$ is a moiety selected from the group consisting of:

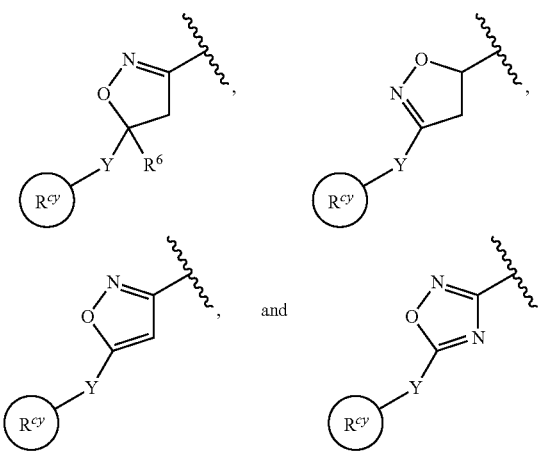

and

9. The compound of claim 8 or a pharmaceutically acceptable salt thereof, wherein $R^1$ is selected from the group consisting of:

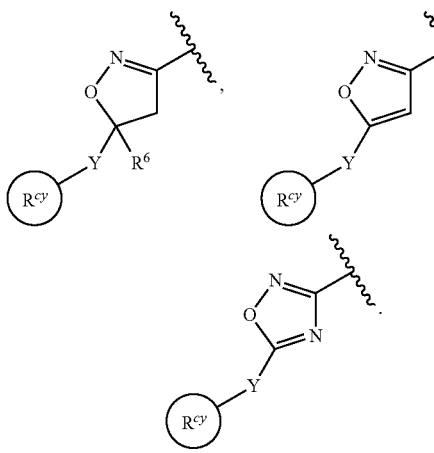

10. The compound of claim 8 or a pharmaceutically acceptable salt thereof, wherein Y is a direct bond, —CH$_2$—, or

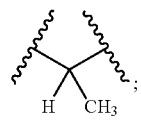

and $R^{cy}$ is phenyl, indanyl, or benzoxazolyl.

11. The compound of claim 1 or a pharmaceutically acceptable salt thereof, wherein M is a bond or —CH$_2$—.

12. The compound of claim 1 or a pharmaceutically acceptable salt thereof, wherein Z is a bond and the subscript n is 4.

13. The compound of claim 1 or a pharmaceutically acceptable salt thereof, wherein $R^4$ is —OH or

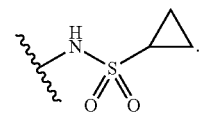 [SMILES: *NS(=O)(=O)C1CC1]

14. The compound of claim 1 or a pharmaceutically acceptable salt thereof, wherein $R^{q1}$, $R^{q2}$, $R^{q3}$, and $R^{q4}$ are each H.

15. The compound of claim 1 or a pharmaceutically acceptable salt thereof, wherein the compound has the Formula (IA),

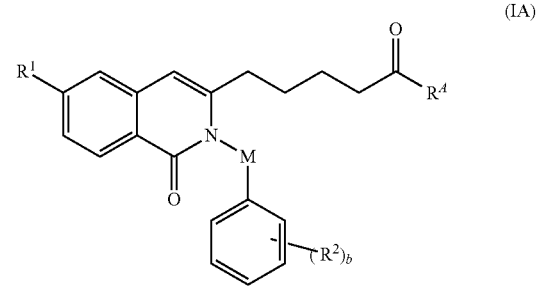

wherein
$R^4$ is —OH or

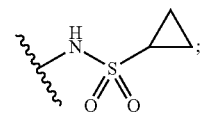 [SMILES: *NS(=O)(=O)C1CC1]

M is a bond or —CH$_2$—; and
$R^1$, $R^2$, and the subscript b are as set forth in claim 1.

16. The compound of claim 1 or a pharmaceutically acceptable salt thereof, wherein the compound is selected from the group consisting of:
  5-(2-(4-fluorophenyl)-6-((1-(4-fluorophenyl)ethyl)carbamoyl)-1-oxo-1,2-dihydroisoquinolin-3-yl)pentanoic acid;
  5-(6-((6-fluoro-1,2,3,4-tetrahydronaphthalen-1-yl)carbamoyl)-2-(4-fluorophenyl)-1-oxo-1,2-dihydroisoquinolin-3-yl)pentanoic acid;
  3-(5-(cyclopropanesulfonamido)-5-oxopentyl)-N-(6-fluoro-1,2,3,4-tetrahydronaphthalen-1-yl)-2-(4-fluorophenyl)-1-oxo-1,2-dihydroisoquinoline-6-carboxamide;

5-(2-(4-fluorophenyl)-6-(2-methyl-4-phenylpiperazine-1-carbonyl)-1-oxo-1,2-dihydroisoquinolin-3-yl)pentanoic acid;

5-(6-(5-(4-fluorobenzyl)isoxazol-3-yl)-2-(4-fluorophenyl)-1-oxo-1,2-dihydroisoquinolin-3-yl)pentanoic acid;

5-(6-(5-(4-fluorobenzyl)-1,2,4-oxadiazol-3-yl)-2-(4-fluorophenyl)-1-oxo-1,2-dihydroisoquinolin-3-yl)pentanoic acid; and N-(cyclopropylsulfonyl)-5-(6-(5-(4-fluorobenzyl)isoxazol-3-yl)-2-(4-fluorophenyl)-1-oxo-1,2-dihydroisoquinolin-3-yl)pentanamide.

17. A pharmaceutical formulation comprising a therapeutically effective amount of the compound of claim 1 or a pharmaceutically acceptable salt thereof, and a pharmaceutically acceptable carrier.

18. A method for treating a disease or condition selected from asthma, allergic rhinitis, or COPD comprising administering to a patient in need of such treatment a therapeutically amount of a compound of claim 1 or a pharmaceutically acceptable salt thereof.

19. A method for treating asthma comprising administering to a patient in need of such treatment a therapeutically amount of a compound of claim 1 or a pharmaceutically acceptable salt thereof and montelukast.

* * * * *